US011553948B2

(12) United States Patent
Haller et al.

(10) Patent No.: US 11,553,948 B2
(45) Date of Patent: Jan. 17, 2023

(54) BONE FIXATION DEVICES, SYSTEMS, AND METHODS

(71) Applicant: University of Utah Research Foundation, Salt Lake City, UT (US)

(72) Inventors: Justin Haller, Salt Lake City, UT (US); T. Wade Fallin, Hyde Park, UT (US); Colin S. Gregersen, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 78 days.

(21) Appl. No.: 17/325,795

(22) Filed: May 20, 2021

(65) Prior Publication Data

US 2022/0370104 A1   Nov. 24, 2022

(51) Int. Cl.
*A61B 17/86* (2006.01)
*A61B 17/72* (2006.01)
*A61B 17/68* (2006.01)

(52) U.S. Cl.
CPC ...... *A61B 17/7208* (2013.01); *A61B 17/8665* (2013.01); *A61B 2017/681* (2013.01)

(58) Field of Classification Search
CPC ............ A61B 17/7208; A61B 17/8665; A61B 2017/681; F16B 19/02; Y10T 403/46
USPC ....... 606/254, 257, 259, 260, 261, 264, 275, 606/62, 65, 67, 301, 304, 323, 328, 105; 411/338; 403/256–261
See application file for complete search history.

(56) References Cited

U.S. PATENT DOCUMENTS 1,194,792 A * 8/1916 Stewart ..................... F16B 5/02
411/338
2,485,531 A   10/1949 Dzus
(Continued)

FOREIGN PATENT DOCUMENTS

CN   202843773 U   4/2013
DE   202007017159 U1   6/2008
(Continued)

OTHER PUBLICATIONS

Zimmer, NCB Periprosthetic Femur Plate System Surgical Technique, (2015) 56 pp.
(Continued)

*Primary Examiner* — Eduardo C Robert
*Assistant Examiner* — David C Comstock
(74) *Attorney, Agent, or Firm* — David Meibos; Maywood IP Law

(57) ABSTRACT

A bone fixation assembly may include a male member removably couplable with a female member. The male member may include a male load-sharing feature having at least one male load-sharing surface. The female member may include a female load-sharing feature having at least one female load-sharing surface. The female load-sharing feature may be positioned and shaped to receive the male load-sharing feature therein. In response to a bending load acting on the bone fixation assembly, at least one of the male member and the female member may bend such that, at least a portion of the at least one male load-sharing surface engages with at least a portion of the at least one female load-sharing surface to distribute the bending load between the male member and the female member.

20 Claims, 19 Drawing Sheets

(56) References Cited

U.S. PATENT DOCUMENTS

| | | |
|---|---|---|
| 2,489,870 A | 11/1949 | Dzus |
| 2,511,051 A | 6/1950 | Dzus |
| 2,560,110 A * | 7/1951 | Horn ...................... B42F 13/00 411/338 |
| 3,489,143 A | 1/1970 | Halloran |
| 3,709,218 A | 1/1973 | Halloran |
| 3,900,025 A | 8/1975 | Barnes, Jr. |
| 4,456,005 A | 6/1984 | Lichty |
| 4,858,601 A | 8/1989 | Glisson |
| 5,250,049 A | 10/1993 | Michael |
| 5,800,436 A | 9/1998 | Lerch |
| 6,010,505 A | 1/2000 | Asche et al. |
| 6,050,819 A | 4/2000 | Robinson |
| 6,146,384 A | 11/2000 | Lee et al. |
| 6,302,887 B1 | 10/2001 | Spranza et al. |
| 6,368,319 B1 | 4/2002 | Schaefer |
| 6,517,543 B1 | 2/2003 | Berrevoets et al. |
| 6,635,059 B2 | 10/2003 | Randall et al. |
| 6,902,567 B2 | 6/2005 | Del Medico |
| 6,908,469 B2 | 6/2005 | Sellers et al. |
| 6,918,912 B2 | 7/2005 | Seemann |
| 7,048,737 B2 | 5/2006 | Wellisz et al. |
| 7,235,090 B2 | 6/2007 | Buckman et al. |
| 7,347,861 B2 | 3/2008 | Johnstone |
| 7,582,107 B2 | 9/2009 | Trail et al. |
| 7,625,395 B2 | 12/2009 | Muckter |
| 8,187,308 B2 | 5/2012 | Mullaney et al. |
| 8,357,186 B2 | 1/2013 | Hadi |
| 8,425,574 B2 | 4/2013 | Huebner et al. |
| 8,585,744 B2 | 11/2013 | Duggal et al. |
| 8,882,816 B2 | 11/2014 | Kartalian et al. |
| 9,011,501 B2 | 4/2015 | Mikhail et al. |
| 9,011,503 B2 | 4/2015 | Duggal et al. |
| 9,138,219 B2 | 9/2015 | Horrell et al. |
| 9,247,963 B2 | 2/2016 | Kollmer |
| 9,320,553 B2 | 4/2016 | Katrana et al. |
| 9,700,359 B2 | 7/2017 | Hatch et al. |
| 9,775,648 B2 | 10/2017 | Greenberg et al. |
| 9,788,862 B2 | 10/2017 | Mootien et al. |
| 9,839,455 B2 | 12/2017 | Cole |
| 9,872,712 B2 | 1/2018 | Trieu |
| 9,980,762 B2 | 5/2018 | Anapliotis |
| 10,039,579 B2 | 8/2018 | Medoff et al. |
| 10,307,245 B2 | 6/2019 | Blacklidge |
| 10,588,679 B2 | 3/2020 | Kukla et al. |
| 10,786,292 B2 | 9/2020 | Singh et al. |
| 10,792,082 B2 | 10/2020 | Zander et al. |
| 10,828,067 B2 | 11/2020 | Katrana et al. |
| 2003/0040746 A1 | 2/2003 | Mitchell et al. |
| 2003/0069582 A1 | 4/2003 | Culbert |
| 2003/0135212 A1 | 7/2003 | Chow |
| 2004/0172029 A1 | 9/2004 | Lerch |
| 2006/0271054 A1 * | 11/2006 | Sucec ................ A61B 17/8685 606/328 |
| 2007/0014649 A1 | 1/2007 | James |
| 2009/0228049 A1 | 9/2009 | Park |
| 2010/0152786 A1 | 6/2010 | Behrbalk |
| 2010/0318086 A1 | 12/2010 | Winemaker |
| 2012/0172936 A1 | 7/2012 | Horrell et al. |
| 2012/0197311 A1 * | 8/2012 | Kirschman ........ A61B 17/7098 606/104 |
| 2012/0226322 A1 | 9/2012 | Gonzalez-Hernandez |
| 2013/0096559 A1 | 4/2013 | Katrana et al. |
| 2016/0038186 A1 | 2/2016 | Herzog et al. |
| 2016/0135861 A1 * | 5/2016 | Kollmer ................ A61B 50/20 606/324 |
| 2016/0242824 A1 * | 8/2016 | Kirschman ........ A61B 17/7068 |
| 2016/0256207 A1 | 9/2016 | Zander et al. |
| 2017/0112552 A1 * | 4/2017 | Sinnott ............. A61B 17/7233 |
| 2020/0146674 A1 | 5/2020 | Bonutti et al. |
| 2020/0146721 A1 | 5/2020 | Sadiq |

FOREIGN PATENT DOCUMENTS

| | | |
|---|---|---|
| EP | 1679044 A2 | 7/2006 |
| GB | 2324964 A | 11/1998 |
| GB | 2457740 A | 8/2009 |
| WO | WO2009125085 A2 | 10/2009 |
| WO | WO2017077489 A1 | 5/2017 |

OTHER PUBLICATIONS

Stryker, T2 Femoral Nailing System Operative Technique, (2016) 56 pp.

International Search Report and Written Opinion dated Aug. 4, 2022 for corresponding PCT Application No. PCT/US2022/029333.

* cited by examiner

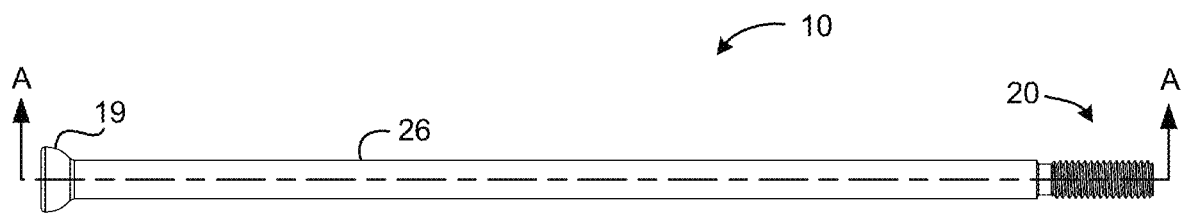
FIG. 2A
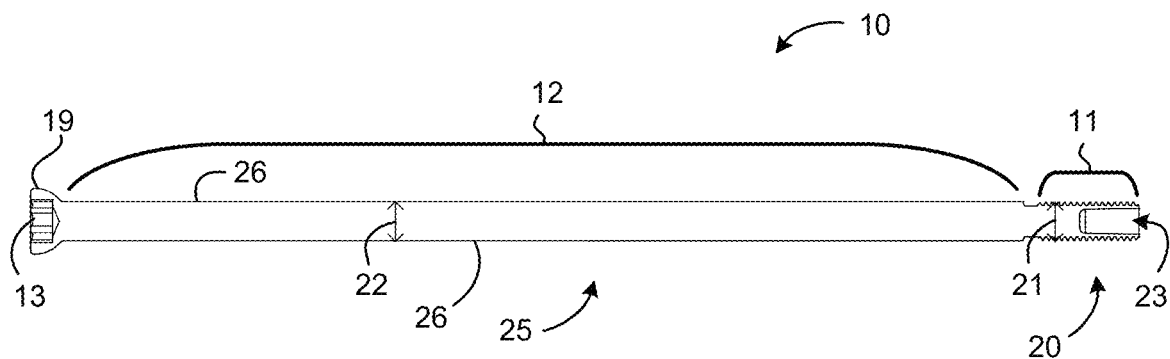
FIG. 2B
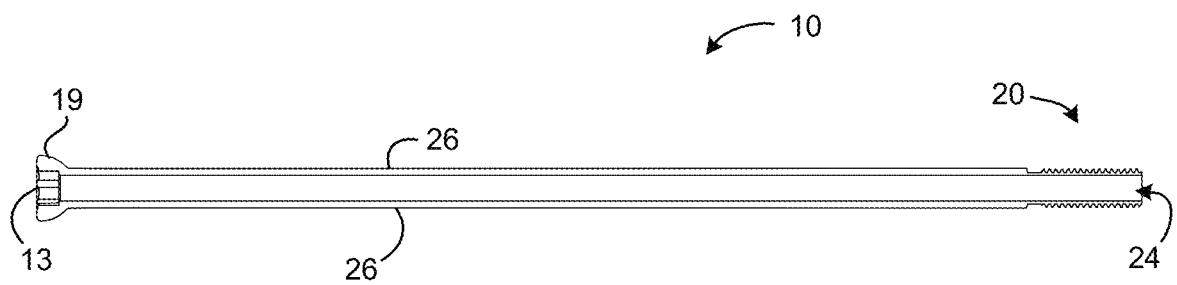
FIG. 2C
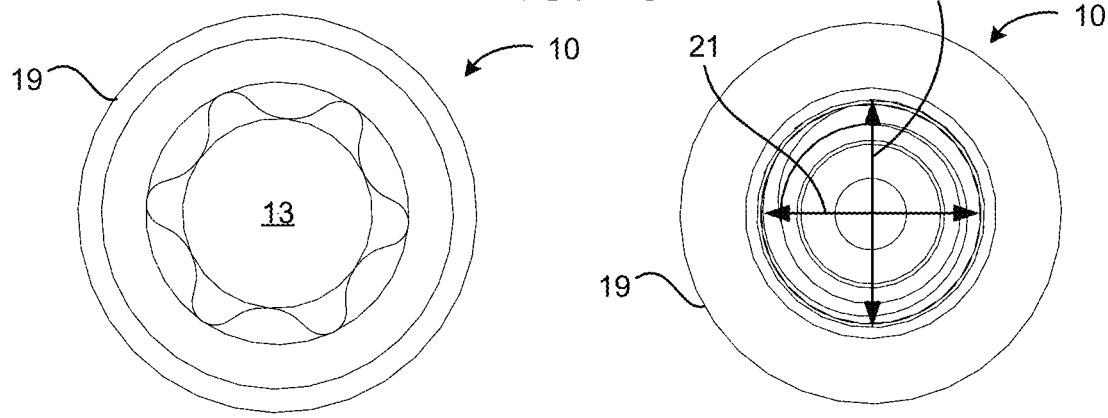
FIG. 2D  FIG. 2E

Table 1: Example Bone Fixation Assembly Dimensions

| Example Bone Fixation Assembly Dimensions of the Present Disclosure | | | | Example Dimensions for Comparably Sized Bone Screws | | |
|---|---|---|---|---|---|---|
| Size (mm) | Male O.D. (mm) | Female O.D. (mm) | Length | Shank O.D. (mm) | Thread O.D. (mm) | Length |
| 2.0 | 1.3 | 2.0 | Continuously adjustable length over a 5mm range | 1.3 | 2.0 | Discrete lengths available in 5mm increments |
| 2.5 | 1.7 | 2.5 | | 1.7 | 2.5 | |
| 3.0 | 2.1 | 3.0 | Continuously adjustable length over a 10mm range | 2.1 | 3.0 | |
| 3.5 | 2.4 | 3.5 | | 2.4 | 3.5 | |
| 4.0 | 2.9 | 4.0 | | 2.9 | 4.0 | |
| 4.5 | 3.0 | 4.5 | | 3.0 | 4.5 | |
| 5.0 | 3.5 | 5.0 | | 3.5 | 5.0 | |
| 6.0 | 4.0 | 6.0 | Continuously adjustable length over a 15mm range | 4.0 | 6.0 | |
| 7.0 | 5.0 | 7.0 | | 5.0 | 7.0 | |
| 8.0 | 6.0 | 8.0 | | 6.0 | 8.0 | |

O.D. = Outside Diamter

FIG. 21

BONE FIXATION DEVICES, SYSTEMS, AND METHODS

TECHNICAL FIELD

The present disclosure relates to bone fixation devices, systems, and methods. More specifically, the present disclosure relates to bone fixation devices, systems, and methods for stabilizing one or more portions of bone.

BACKGROUND

Surgical procedures involving fixation of bone portions with bone screws and fasteners can fail or become lose over time due to bending loads, multi-axial forces, and/or off-axis loading scenarios that may be applied to the bone screws during the healing process. Existing bone screws and fasteners may not provide sufficient fixation and strength to overcome these bending loads, multi-axial forces, and/or off-axis loading scenarios.

Accordingly, bone fixation devices, systems, and methods with improved fixation, strength, and load sharing characteristics would be desirable.

SUMMARY

The various bone fixation devices, systems, and methods of the present disclosure have been developed in response to the present state of the art, and in particular, in response to the problems and needs in the art that have not yet been fully solved by currently available bone fixation devices, systems, and methods. In some embodiments, the bone fixation devices, systems, and methods of the present disclosure may provide improved bone fixation and stabilization between two or more bone portions.

In some embodiments, a bone fixation assembly may include a male member and a female member. The male member may include a male member shaft having a proximal end, a distal end, and a first longitudinal axis. The male member may also include a first bone engaging feature at the proximal end of the male member shaft, an external thread portion at the distal end of the male member shaft, the external thread portion having a first length and a first major diameter, and a male load-sharing feature intermediate the first bone engaging feature and the external thread portion. The male load-sharing feature may have a second length and an outer diameter defining at least one male load-sharing surface. The female member may include a female member shaft having a proximal end, a distal end, and a second longitudinal axis. The female member may also include: a second bone engaging feature at the proximal end of the female member shaft; an internal thread portion having a third length and a second major diameter, the internal thread portion configured to receive the external thread portion of the male member to removably couple the male member with the female member; and a female load-sharing feature located distal to the internal thread portion and extending between the internal thread portion and the distal end of the female member shaft, the female load-sharing feature having a fourth length and an inner diameter defining at least one female load-sharing surface, the female load-sharing feature positioned and shaped to receive the male load-sharing feature therein. Moreover, when the bone fixation assembly is implanted in a bone, at least a portion of the at least one male load-sharing surface may be positioned adjacent to at least a portion of the at least one female load-sharing surface.

In some embodiments of the bone fixation assembly, at least one of the at least one male load-sharing surface and the at least one female load-sharing surface may comprise a cylindrical surface.

In some embodiments of the bone fixation assembly, the male load-sharing feature may be configured to slide and rotate within the female load-sharing feature during assembly of the male member to the female member.

In some embodiments of the bone fixation assembly, at least one of the male member and the female member may comprise a low tensile modulus material that is configured to provide a compression force to the bone.

In some embodiments of the bone fixation assembly, the male member may comprise one of: a male member blind bore, a male member through bore, and a self-centering tip.

In some embodiments of the bone fixation assembly, at least one of the male member and the female member may include a bone retention feature.

In some embodiments of the bone fixation assembly, the male member may comprise a male member head having a first torque connection interface, and the female member may comprise a female member head having a second torque connection interface.

In some embodiments, a bone fixation assembly may include a male member and a female member. The male member may include a male member shaft having a proximal end, a distal end, and a first longitudinal axis. The male member may also include a first bone engaging feature at the proximal end of the male member shaft, an external thread portion at the distal end of the male member shaft, the external thread portion having a first length and a first major diameter, and a male load-sharing feature intermediate the first bone engaging feature and the external thread portion. The male load-sharing feature may have a second length and an outer diameter defining at least one male load-sharing surface. The female member may include a female member shaft having a proximal end, a distal end, and a second longitudinal axis. The female member may also include: a second bone engaging feature at the proximal end of the female member shaft; an internal thread portion having a third length and a second major diameter, the internal thread portion configured to receive the external thread portion of the male member to removably couple the male member with the female member when the bone fixation assembly is implanted in a bone; and a female load-sharing feature located distal to the internal thread portion and extending between the internal thread portion and the distal end of the female member shaft, the female load-sharing feature having a fourth length and an inner diameter defining at least one female load-sharing surface, the female load-sharing feature positioned and shaped to receive the male load-sharing feature therein. Moreover, the outer diameter of the male load-sharing feature may be greater than or equal to the first major diameter of the external thread portion.

In some embodiments of the bone fixation assembly, the male member may comprise a male member head having a first torque connection interface, and the female member may comprise a female member head having a second torque connection interface.

In some embodiments of the bone fixation assembly, at least one of the first bone engaging feature and the second bone engaging feature may comprise a partially spherical surface that may be integrally formed with the male member head and/or female member head, respectively.

In some embodiments of the bone fixation assembly, the male member head and the female member head may comprise first partially spherical surfaces, and the first bone engaging feature and the second bone engaging feature may comprise second partially spherical surfaces that may be configured to mate with the first partially spherical surfaces to allow polyaxial articulation of the first bone engaging feature and the second bone engaging feature with respect to the male member head and the female member head.

In some embodiments of the bone fixation assembly, at least one of the first bone engaging feature and the second bone engaging feature may comprise a washer.

In some embodiments of the bone fixation assembly, at least one of the first bone engaging feature and the second bone engaging feature may comprise a bone plate, and the bone fixation assembly may also include a retention cap configured to couple with the bone plate. One or more retention surfaces of the retention cap may be configured to engage with at least one of the male member head and the female member head to adjust a space between the first bone engaging feature and the second bone engaging feature.

In some embodiments of the bone fixation assembly, the inner diameter of the female load sharing feature may be greater than or equal to the second major diameter of the internal thread portion.

In some embodiments of the bone fixation assembly, at least one of the at least one male load-sharing surface and the at least one female load-sharing surface may comprise a cylindrical surface.

In some embodiments, a bone fixation assembly may include a male member and a female member. The male member may include a male member shaft having a proximal end, a distal end, and a first longitudinal axis. The male member may also include a first bone engaging feature at the proximal end of the male member shaft, an external thread portion at the distal end of the male member shaft, the external thread portion having a first length and a first major diameter, and a male load-sharing feature intermediate the first bone engaging feature and the external thread portion. The male load-sharing feature may have a second length and an outer diameter defining at least one male load-sharing surface. The female member may include a female member shaft having a proximal end, a distal end, and a second longitudinal axis. The female member may also include: a second bone engaging feature at the proximal end of the female member shaft; an internal thread portion having a third length and a second major diameter, the internal thread portion configured to receive the external thread portion of the male member to removably couple the male member with the female member; and a female load-sharing feature located distal to the internal thread portion and extending between the internal thread portion and the distal end of the female member shaft, the female load-sharing feature having a fourth length and an inner diameter defining at least one female load-sharing surface, the female load-sharing feature positioned and shaped to receive the male load-sharing feature therein. Moreover, in response to a bending load acting on the bone fixation assembly after implantation in a bone, at least one of the male member and the female member bend such that, at least a portion of the at least one male load-sharing surface engages with at least a portion of the at least one female load-sharing surface to distribute the bending load between the male member and the female member.

In some embodiments of the bone fixation assembly, at least one of the male member and the female member may comprise a bone retention feature.

In some embodiments of the bone fixation assembly, the bone retention feature may comprise one or more barbs.

In some embodiments of the bone fixation assembly, the bone retention feature may comprise a thread.

In some embodiments of the bone fixation assembly, the thread may comprise at least one of a right-handed thread and a left-handed thread.

In some embodiments of the bone fixation assembly, the inner diameter of the female load sharing feature may be greater than or equal to the second major diameter of the internal thread portion.

These and other features and advantages of the present disclosure will become more fully apparent from the following description and appended claims, or may be learned by the practice of the devices, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIG. 2A illustrates a side view of the male member of the bone fixation assembly shown in FIG. 1;

FIG. 2B illustrates a cross-sectional side view of the male member of FIG. 2A comprising a blind bore taken along the line A-A in FIG. 2A;

FIG. 2C illustrates a cross-sectional side view of the male member of FIG. 2A comprising a male member through bore taken along the line A-A in FIG. 2A;

FIG. 2D illustrates a proximal end view of the male member of FIG. 2A;

FIG. 2E illustrates a distal end view of the male member of FIG. 2A;

FIG. 21 is a table illustrating some non-limiting example dimensions that may be utilized with the bone fixation assemblies of present disclosure.

Figure 1:
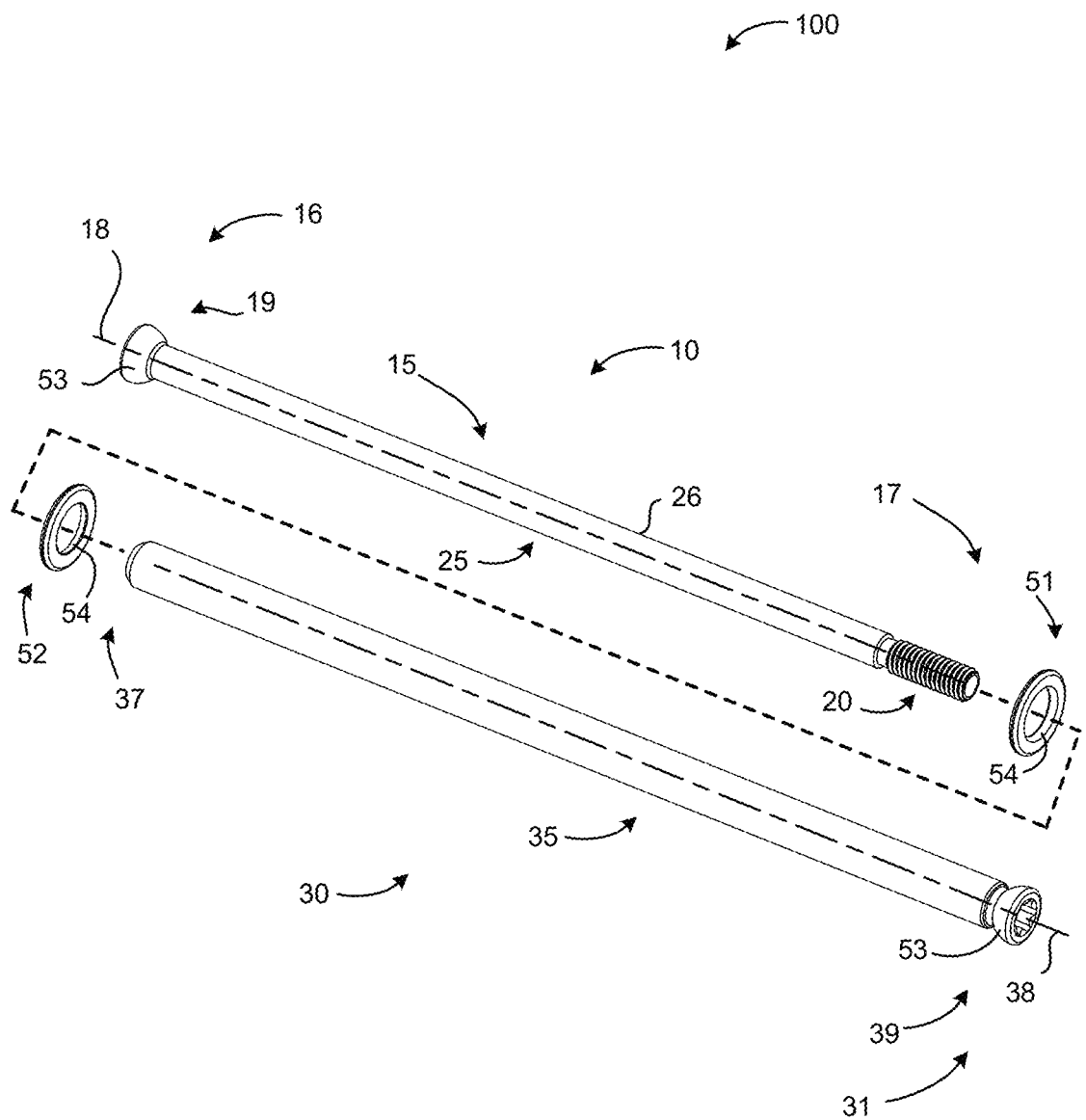
FIG. 1 illustrates an exploded perspective view of a bone fixation assembly, according to an embodiment of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure, but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The following examples have been included to provide guidance to one of ordinary skill in the art for practicing representative embodiments of the presently disclosed subject matter. In light of the present disclosure and the general level of skill in the art, those of skill in the art can appreciate that the following examples are intended to be exemplary only and that numerous changes, modifications, and alterations can be employed without departing from the scope of the presently disclosed subject matter.

Fixation of bone portions with bone screws may be utilized in a variety of surgical procedures including, but not limited to: trauma fixation, arthrodesis, osteotomies, etc. For example, in trauma fixation procedures, high-energy events can cause bones to break and fragment. Bone screws may be utilized to secure the bone fragments in a correct anatomic alignment while the bone heals. Arthrodesis procedures can treat degenerative bone joints, which may cause pain and loss of joint function, by removing degraded articular cartilage from a bone joint and then holding the bone joint in compression with bone screws while the bones fuse together across the joint. Osteotomy procedures can realign a bone to a more favorable position, by first cutting the bone and then using bone screws to hold the cut bone portions in a new desired alignment while the bone heals.

Three example surgical techniques utilizing bone screws include: (1) a lag screw technique; (2) a positional screw technique; and (3) a compression screw technique. A bone screw utilized in a lag screw technique may include a thread at a distal end of the bone screw with a smooth shank extending between a head of the bone screw and the distal thread (e.g., a partially threaded bone screw). A bone screw utilized in a positional screw technique may include a thread that extends from a head of the bone screw to a distal end of the bone screw (e.g., a fully threaded bone screw). A bone screw utilized in a compression screw technique may include a first thread having a first thread pitch located at a distal end of the bone screw, and a second thread having a second thread pitch located at a proximal end of the bone screw. The first thread pitch may be greater than the second thread pitch to achieve compression. Partially threaded bone screws, fully threaded bone screws, and compression bone screws may be available in solid and cannulated versions. A cannulated version may enable guided insertion of a bone screw over a K-wire or pin.

In the lag screw technique, the head of the bone screw may contact a proximal surface of a first bone portion, the shank of the bone screw may extend through the first bone portion, and the distal thread of the bone screw may engage a second bone portion. When the head of the bone screw contacts the proximal surface of the first bone portion (also referred to herein as "fully seated"), continued rotation of the bone screw about its longitudinal axis will draw the first and second bone portions toward each other, thereby "lagging" the two bone portions toward each other.

In the positional screw technique, a fully threaded bone screw may be placed within two bone portions. Continued rotation of the bone screw about its longitudinal axis after it has been fully seated will not induce any relative movement between each bone portion, thereby maintaining the relative position of each bone portion with respect to each other.

In the compression screw technique, the distal threads of the compression bone screw may be advanced through a first bone portion and into a second bone portion. Then, as the proximal threads of the compression bone screw enter into the surface of the first bone portion, continued rotation of the bone screw about its longitudinal axis will move the two bone portions toward each other due to the difference in thread pitch between the proximal and distal threads. Once the proximal thread is fully seated in the bone, a predetermined amount of displacement between the two bone portions is achieved based on the length of the proximal thread and the difference in pitch between the proximal and distal threads.

The foregoing bone screw surgical techniques have a number of clinical challenges and shortcomings. For example, one study investigated the incidence rate of bone screw thread stripping in a mechanical analog of cancellous bone (Stoesz M J, et al. Surgeon perception of cancellous screw fixation. Journal of Orthopaedic Trauma. 2014). This reference is incorporated by reference herein in its entirety. The mechanical analog model in this study simulated the condition of bone screw insertion into poor quality bone, as is the case in patients with osteopenia or osteoporosis. In this setting, surgeons must rely on tactile feedback to achieve the desired level of compression and thread purchase without stripping the threads. This study found that surgeons induced thread stripping 45% of the time and, when the threads were stripped, 90% of the time the surgeon was not aware that the threads had stripped. Thus, there is a need for a stronger, more reliable means of obtaining screw purchase within bone.

Another shortcoming with the foregoing bone screw surgical techniques is the risk of bone screw loosening and loss of fixation of the bone portions during the post-operative period while the bone is healing. In an illustrative bone screw surgical procedure, a study reported on the incidence rate of bone screw loosening and bone fixation failure in 110 patients where partially threaded cannulated bone screws were utilized to stabilize sacral fractures and sacroiliac joint dislocations (Kim J W, et al. The incidence of and factors affecting iliosacral screw loosening in pelvic ring injury. Archive of Orthopaedic and Trauma Surgery. 2016). This reference is incorporated by reference herein in its entirety. This study showed bone screw loosening in 19 patients (17.3%), and of those, 13 patients (11.8%) had failure of bone fixation requiring reoperation. Thus, stronger bone fixation constructs with greater bone purchase for reducing the incidence rate of bone screw loosening and subsequent loss of bone fixation would be desirable.

The following disclosure presents various bone fixation devices, systems, and methods for utilization in bone and other tissues as implantable devices (e.g., orthopedic implants, spine implants, sports medicine implants, trauma implants, reconstruction implants, extremity implants, veterinary implants, etc.).

Example applications/procedures that may utilize any of the fixation devices described or contemplated herein, in any configuration and with any of the features described herein, may include, but are not limited to: trauma procedures (e.g., fracture fixation, etc.), post-traumatic reconstruction (pelvic or joint fusions), spine procedures (e.g., SI fusion, facet fixation, etc.), joint reconstruction procedures (total hip arthroplasty, total knee arthroplasty), sports related procedures, extremity procedures, cranio-maxillo-facial procedures, rib plating procedures, veterinary procedures, bone plating procedures (e.g., femur plates, humerus plates, tibial plates, etc.), intramedullary nail fixation procedures, amputee connection procedures, sarcoma procedures, shoulder/glenoid fixation, small bone fixation, correction, or fusion (e.g., foot/ankle, hand/wrist, etc.), joint fusions, osteotomies, procedures involving osteoporotic or compromised bone, etc.

It will be understood that any feature of any bone fixation assembly described or contemplated herein may be combined with any other bone fixation assembly that is described or contemplated herein without departing from the spirit or scope of the present disclosure.

Figure 3A:
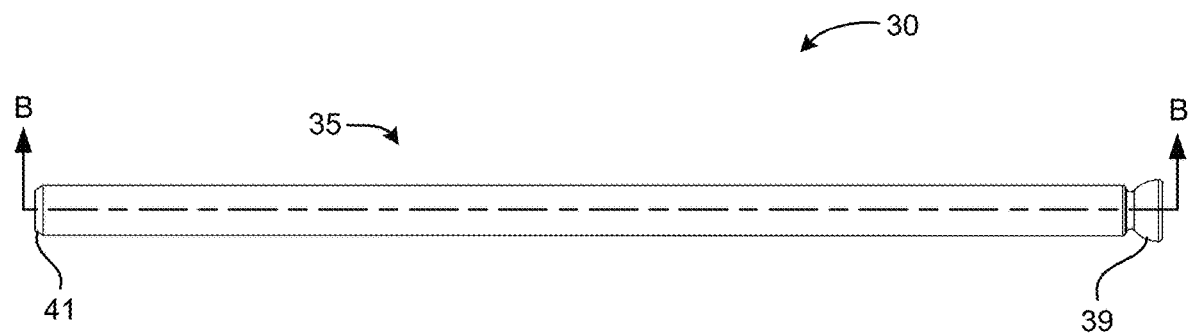
FIG. 3A illustrates a side view of the female member of the bone fixation assembly shown in FIG. 1.
Figure 3B:
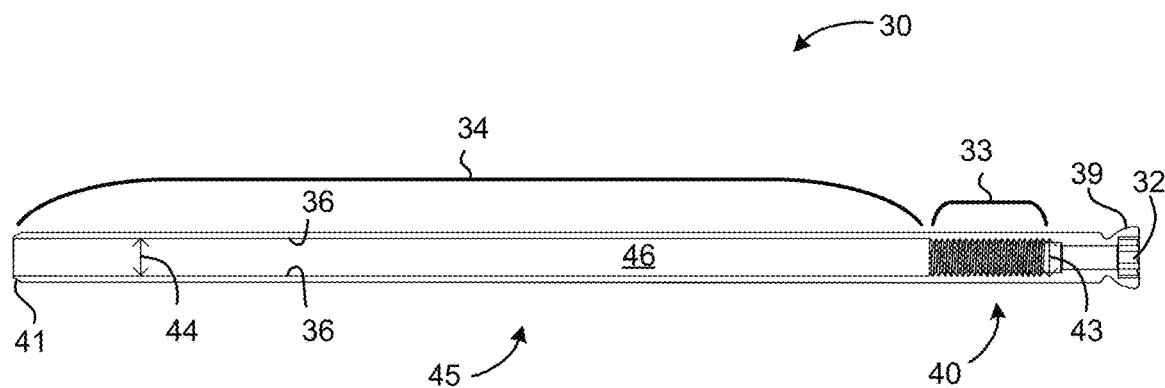
FIG. 3B illustrates a cross-sectional side view of the female member of FIG. 3A taken along the line B-B in FIG. 3A.
Figure 3C:
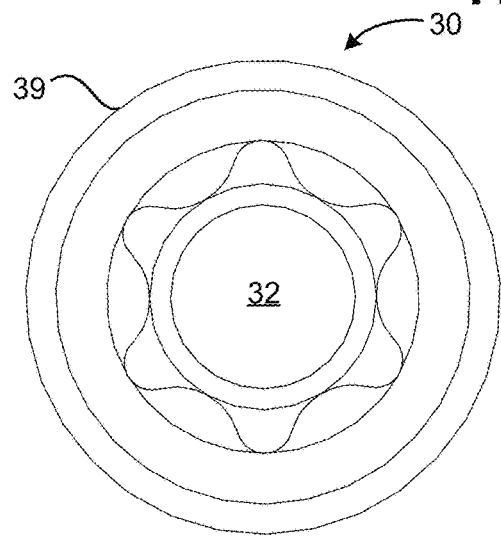
FIG. 3C illustrates a proximal end view of the female member of FIG. 3A.
Figure 3D:
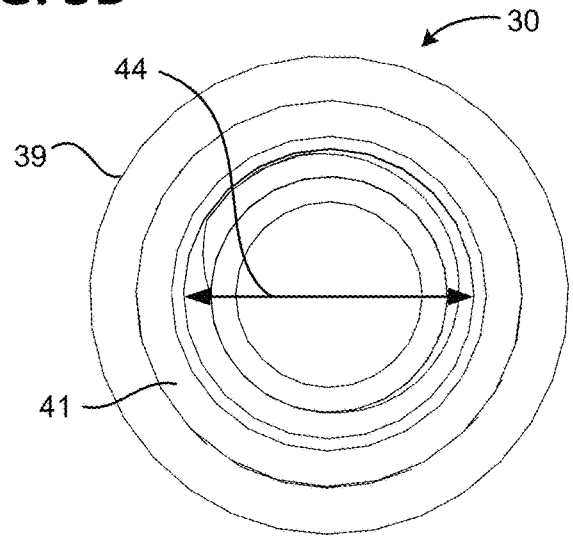
FIG. 3D illustrates a distal end view of the female member of FIG. 3A.
Figure 4A:
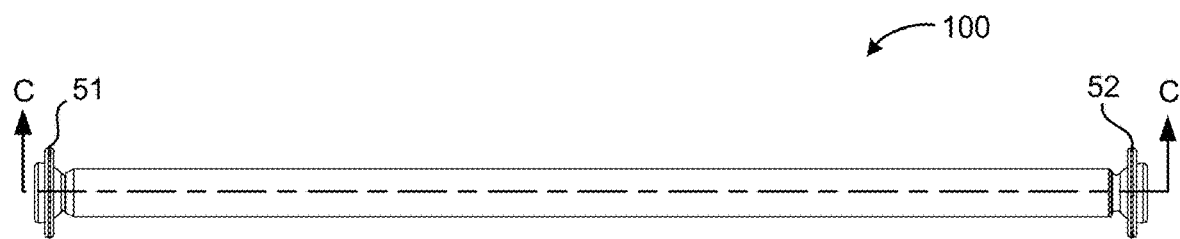
FIG. 4A illustrates a side view of the bone fixation assembly of FIG. 1 in assembled form.
Figure 4B:
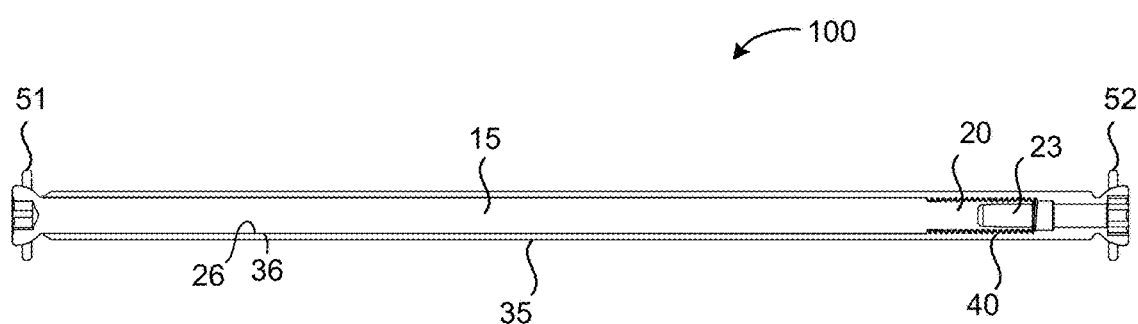
FIG. 4B illustrates a cross-sectional side view of the bone fixation assembly of FIG. 4A comprising a male member blind bore taken along the line C-C in FIG. 4A.
Figure 4C:
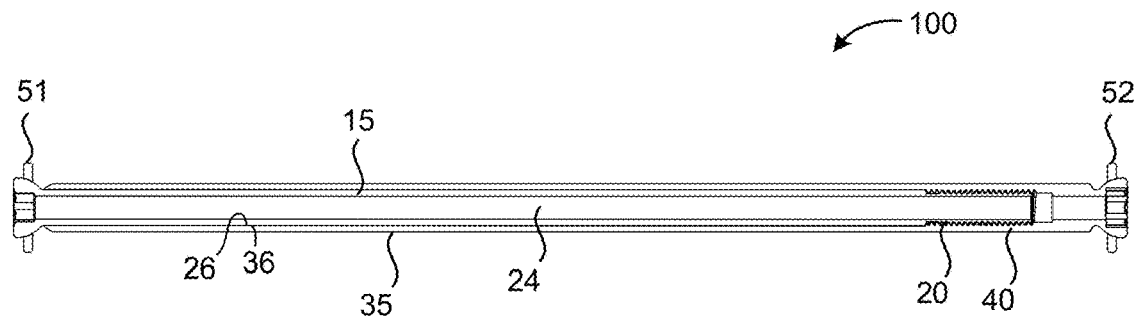
FIG. 4C illustrates a cross-sectional side view of the bone fixation assembly of FIG. 4A comprising a male member through bore taken along the line C-C in FIG. 4A.
Figure 4D:
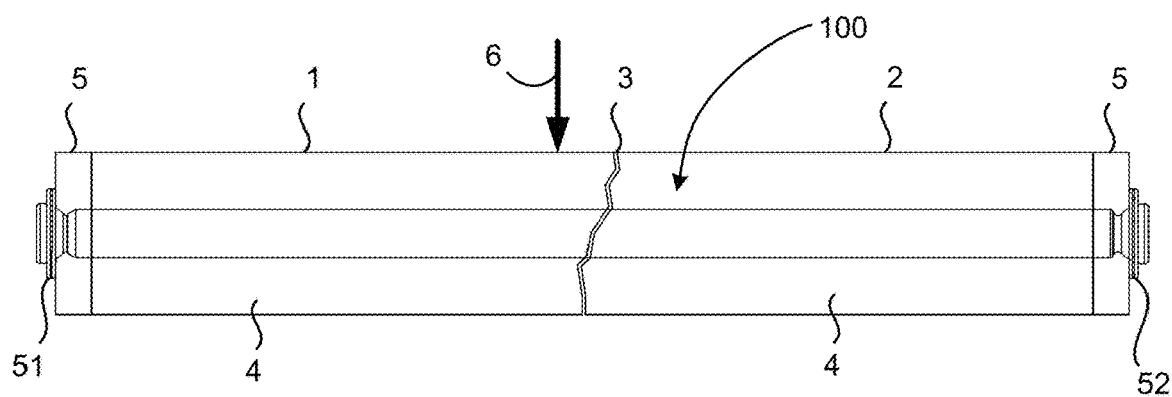
FIG. 4D illustrates a side view of the bone fixation assembly of FIG. 4A implanted in bone.

FIGS. 1-4D illustrate various views of a bone fixation assembly 100 and its components, according to an embodiment of the present disclosure. Specifically, FIG. 1 is an exploded perspective view of the bone fixation assembly 100; FIG. 2A is a side view of a male member 10 of the bone fixation assembly 100; FIG. 2B is a cross-sectional side view of the male member 10 (including a blind bore 23) that is taken along the line A-A in FIG. 2A; FIG. 2C is a cross-sectional side view of the male member 10 (including a male member through bore 24) that is taken along the line A-A in FIG. 2A; FIG. 2D is a proximal end view of the male member 10; FIG. 2E is a distal end view of the male member 10; FIG. 3A is a side view of a female member 30 of the bone fixation assembly 100; FIG. 3B is a cross-sectional side view of the female member 30 that is taken along the line B-B in FIG. 3A; FIG. 3C is a proximal end view of the female member 30; FIG. 3D is a distal end view of the female member 30; FIG. 4A is a side view of the bone fixation assembly 100 in assembled form; FIG. 4B is a cross-sectional side view of the bone fixation assembly 100 (with the blind bore 23) that is taken along the line C-C in FIG. 4A; FIG. 4C is a cross-sectional side view of the bone fixation assembly 100 (with the male member through bore 24) that is taken along the line C-C in FIG. 4A; and FIG. 4D is a side view of the bone fixation assembly 100 implanted in bone.

As shown in FIGS. 1-4D, the bone fixation assembly 100 may generally comprise the male member 10, the female member 30, a first bone engaging feature 51, and a second bone engaging feature 52.

As used herein, the phrase "bone engaging feature" may include any structure comprising a surface that is configured to engage a bone.

Accordingly, in some embodiments, the male member 10 and/or the female member 30 may comprise a first bone engaging feature and/or a second bone engaging feature 52. For example, in some embodiments a male member head 19 coupled with the male member 10 may comprise one or more surfaces that may serve as the first bone engaging feature, and a female member head 39 coupled with the female member 30 may comprise one or more surfaces that may serve as the second bone engaging feature. In some embodiments, at least one of the first bone engaging feature and the second bone engaging feature may comprise a partially spherical surface that may be integrally formed with the male member head and/or female member head, as shown in FIG. 1. However, it will also be understood that the male member head 19 and/or the female member head 39 may comprise at least one surface of any shape, size, or configuration suitable for engaging a bone directly, or indirectly through other components, as will be discussed in more detail below.

In the embodiment shown in FIGS. 1-4D, each of the first bone engaging feature 51 and/or the second bone engaging feature 52 may comprise washers. In some embodiments, the washers may comprise a generally circular shape with a central aperture configured to receive the male member 10 and/or the female member 30 therethrough. However, it will also be understood that washers of any shape, size, and configuration may be utilized, including bone plates of any shape, size, and configuration, as will be discussed below in more detail with respect to FIGS. 11A-14B. Moreover, in some embodiments the first bone engaging feature 51 and/or the second bone engaging feature 52 may comprise other structures known in the art that may be utilized to engage a bone including, but not limited to: a tapered external thread (as will be discussed in more detail below), a toggle bar, an expanding mandrel, etc.

In some embodiments, the male member head 19 and/or the female member head 39 may include first partially spherical surfaces 53, and the washers may include second partially spherical surfaces 54 configured to mate with the first partially spherical surfaces 53 to allow polyaxial articulation of the washers with respect to the male member head 19 and/or the female member head 39.

As shown in FIGS. 1-2E, the male member 10 may generally comprise a male member shaft 15, an external thread portion 20, a male load-sharing feature 25, and the male member head 19.

The male member shaft 15 may extend along a first longitudinal axis 18 between a proximal end 16 and a distal end 17 of the male member shaft 15. The male member head 19 may be located at the proximal end 16 of the male member shaft 15, the external thread portion 20 may be located at the distal end 17 of the male member shaft 15, and the male load-sharing feature 25 may be intermediate the male member head 19 and the external thread portion 20.

As previously discussed, the male member head 19 may comprise any shape, size, or configuration suitable for engaging a bone directly, or for coupling with any bone engaging feature described or contemplated herein.

In some embodiments, the male member head 19 may include a first torque connection interface 13 formed in or on the male member head 19, as shown in FIGS. 2B-2D.

In some embodiments, the first torque connection interface 13 may comprise a hexalobular shape, as shown in FIG. 2D. However, it will be understood that the first torque connection interface 13 may comprise any shape, size, or configuration suitable for receiving a torque force from a suitable drive tool having a complementary shape (e.g., see driver tool 98 in FIG. 10G) including, but not limited to: a hex shape, a square shape, a slot, cruciate slots, etc.

As shown in FIG. 2B, the external thread portion 20 may have a first length 11 and a first major diameter 21. The first major diameter 21 may correspond to a major diameter of a thread formed around the external thread portion 20.

In some embodiments, the external thread portion 20 may include a blind bore 23 formed within the external thread portion 20. In some embodiments, the blind bore 23 may extend along at least a portion of the first length 11 of the external thread portion 20.

In some embodiments, the external thread portion 20 may include a self-centering tip (not shown) that may protrude distally from the external thread portion 20. This self-centering tip may be utilized in place of the blind bore 23 and guidewire 90 to insert the male member 10 into a bone tunnel, as will be discussed in more detail below.

In some embodiments, the external thread portion 20 may include a through bore that is formed all the way through the external thread portion 20 and/or the male load-sharing feature 25, as shown in FIG. 2C.

Continuing with FIG. 2B, the male load-sharing feature 25 may have a second length 12 and an outer diameter 22. The outer diameter 22 may define or correspond to at least a portion of the at least one male load-sharing surface 26 of the male load-sharing feature 25.

In some embodiments, the at least one male load-sharing surface 26 may comprise a generally smooth cylindrical surface. However, it will also be understood that the at least one male load-sharing surface 26 may comprise any shape, size, or configuration. For example, in some embodiments the male load-sharing feature 25 and/or the at least one male load-sharing surface 26 may comprise any shape or feature including, but not limited to: one or more ribs, splines, protrusions, recesses, etc., without departing from the spirit or scope of the present disclosure.

In some embodiments, the outer diameter 22 of the male load-sharing feature 25 may be greater than or equal to the first major diameter 21 of the external thread portion 20.

In some embodiments, a diameter corresponding to at least a portion of the at least one male load-sharing surface 26 may be greater than or equal to the first major diameter 21 of the external thread portion 20.

Referring to FIGS. 1 and 3A-3D, the female member 30 may generally comprise a female member shaft 35, an internal thread portion 40, a female load-sharing feature 45, and the female member head 39.

The female member shaft 35 may extend along a second longitudinal axis 38 between a proximal end 31 and a distal end 37 of the female member shaft 35. The female member head 39 may be located at the proximal end 31 of the female member shaft 35, the internal thread portion 40 may be located near the female member head 39, and the female load-sharing feature 45 may be located distal to the internal thread portion 40 and may extend between the internal thread portion 40 and the distal end 37 of the female member shaft 35.

In some embodiments, the internal thread portion 40 may be located distal to the female member head 39, the second bone engaging feature, and/or the second bone retention feature.

In some embodiments, at least a portion of the internal thread portion 40 may be located distal to the female member head 39, the second bone engaging feature, and/or the second bone retention feature.

In some embodiments, at least a portion of the internal thread portion 40 may be located within and/or at least partially pass through the female member head 39, the second bone engaging feature, and/or the second bone retention feature.

In some embodiments, the distal end 37 of the female member shaft 35 may comprise a chamfered surface 41 or a radius edge that may help facilitate insertion of the female member 30 into a bone.

As previously discussed, the female member head 39 may comprise any shape, size, or configuration suitable for engaging a bone directly, or for coupling with any bone engaging feature described or contemplated herein.

In some embodiments, the female member head 39 may include a second torque connection interface 32 formed in or on the female member head 39, as shown in FIGS. 3B and 3C.

In some embodiments, the second torque connection interface 32 may comprise a hexalobular shape, as shown in FIG. 3C. However, it will also be understood that the second torque connection interface 32 may comprise any shape, size, or configuration suitable for receiving a torque force from a drive tool having a complementary shape. including, but not limited to: a hex shape, a square shape, a slot, cruciate slots, etc.

As shown in FIG. 3B, the internal thread portion 40 may have a third length 33 and a second major diameter 43. The second major diameter 43 may correspond to a major diameter of a thread formed within the internal thread portion 40.

In some embodiments, the internal thread portion 40 may be configured to receive the external thread portion 20 of the male member 10 to removably couple the male member 10 with the female member 30.

In some embodiments, the second major diameter 43 of the internal thread portion 40 may be equal to or slightly greater than the first major diameter 21 of the external thread portion 20 in order to receive the thread of the external thread portion 20 within the complementary shaped thread of the internal thread portion 40.

In some embodiments, the thread of the external thread portion 20 and/or the thread of the internal thread portion 40 may be right-hand threaded.

In some embodiments, the thread of the external thread portion 20 and/or the thread of the internal thread portion 40 may be left-hand threaded.

In some embodiments, the internal thread portion 40 may include a female member through bore 46 formed through the internal thread portion 40 and/or the female load-sharing feature 45, as shown in FIG. 3B.

Continuing with FIG. 3B, the female load-sharing feature 45 may have a fourth length 34 and an inner diameter 44.

In some embodiments, the fourth length 34 of the female load-sharing feature 45 may cause the distal end 37 of the female member 30 to engage with the male member head 19 when the bone fixation assembly 100 is fully assembled.

In some embodiments, the fourth length 34 of the female load-sharing feature 45 may cause the distal end 37 of the female member 30 to be located adjacent the male member head 19 (but not engage with the male member head 19) when the bone fixation assembly 100 is fully assembled.

In some embodiments, engagement between the external thread portion 20 and the internal thread portion 40 may allow for a continuous range of infinite adjustment for an overall length of the bone fixation assembly 100. For example, engagement between the external thread portion 20 and the internal thread portion 40 may allow for a range (e.g., +/−3 mm, +/−5 mm, +/−10 mm, +/−15 mm, etc.), over which the overall length of the bone fixation assembly 100 may be continuously/infinitely adjusted in order to fine tune the overall length of the bone fixation assembly 100 to fit a particular bone size or application.

In some embodiments, the inner diameter 44 may at least partially define a surface of the female member through bore 46 within the female load-sharing feature 45. In other words, the inner diameter 44 may define at least a portion of at least one female load-sharing surface 36 within the female load-sharing feature 45.

In some embodiments, the at least one female load-sharing surface 36 may comprise a generally smooth cylindrical surface. However, it will also be understood that the at least one female load-sharing surface 36 may comprise any shape, size, or configuration. For example, in some embodiments the female load-sharing feature 45 and/or the at least one female load-sharing surface 36 may comprise any shape or feature including, but not limited to: one or more ribs, splines, protrusions, recesses, etc., without departing from the spirit or scope of the present disclosure.

In some embodiments, the inner diameter 44 of the female load-sharing feature 45 may be greater than or equal to the second major diameter 43 of the internal thread portion 40.

In some embodiments, the inner diameter 44 of the female load-sharing feature 45 may be greater than or equal to the first major diameter 21 of the external thread portion 20.

In some embodiments, the inner diameter 44 of the female load-sharing feature 45 may be greater than or equal to the outer diameter 22 of the male load-sharing feature 25.

In some embodiments, the inner diameter 44 of the female load-sharing feature 45 may be slightly greater than the outer diameter 22 of the male load-sharing feature 25 to create a very close sliding and/or rotational fit between the female load-sharing feature 45 and the male load-sharing feature 25 during assembly.

In some embodiments, the female load-sharing feature 45 may be positioned and shaped to receive the male load-sharing feature 25 therein such that at least a portion of the at least one male load-sharing surface 26 may be positioned adjacent to at least a portion of the at least one female load-sharing surface 36, as shown in FIGS. 4B and 4C.

FIG. 4D illustrates a side view of the bone fixation assembly 100 implanted within a first bone portion 1 and a second bone portion 2 in order to stabilize each bone portion relative to each other and/or to apply compression to the fracture surface or disunion 3.

In some embodiments, the first bone portion 1 and the second bone portion 2 may each include a cancellous bone region 4 and a cortical bone region 5. The cortical bone region 5 may also include a cortical bone outer surface or cortex.

In some embodiments, the first bone portion 1 and the second bone portion 2 may be separated by at least one bone fracture, fracture line, cut bone surface, fracture surface, or disunion 3 intermediate the first bone portion 1 and the second bone portion 2. However, it will also be understood that any of the bone fixation assemblies described or contemplated herein may be implanted within a single bone or a single tissue, as well as a plurality of bones/bone portions or a plurality of tissues/tissue portions, etc., without departing from the spirit or scope of the present disclosure.

In some embodiments, in response to a bending load 6 (e.g., see FIG. 4D) acting on the first bone portion 1, the second bone portion 2, and/or the bone fixation assembly 100, at least one of the male member 10 and the female member 30 may bend such that, at least a portion of the at least one male load-sharing surface 26 may engage with at least a portion of the at least one female load-sharing surface 36 to distribute the bending load 6 between the male member 10 and the female member 30. In this manner, a relative strength and stiffness of the bone fixation assembly 100 may be increased in comparison to traditional bone screws/fasteners, as will be discussed below in more detail with respect to FIGS. 18 and 19.

Figure 5A:
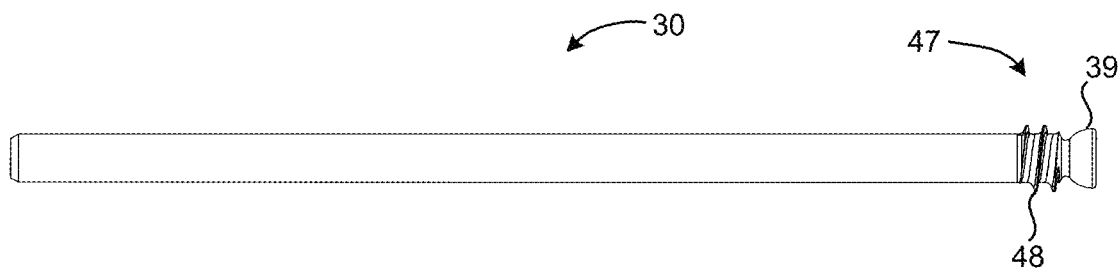
FIG. 5A illustrates a side view of a female member, according to another embodiment of the present disclosure.
Figure 5B:
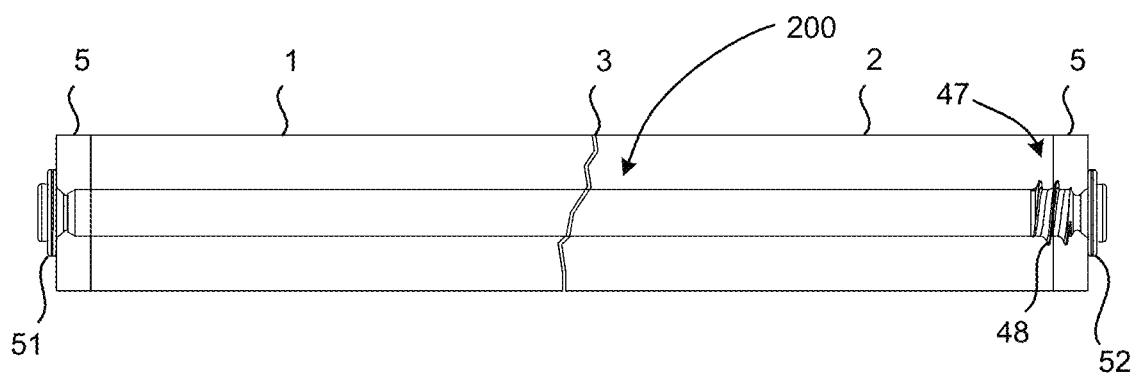
FIG. 5B illustrates a side view of a bone fixation assembly comprising the female member of FIG. 5A implanted in bone.
Figure 6A:
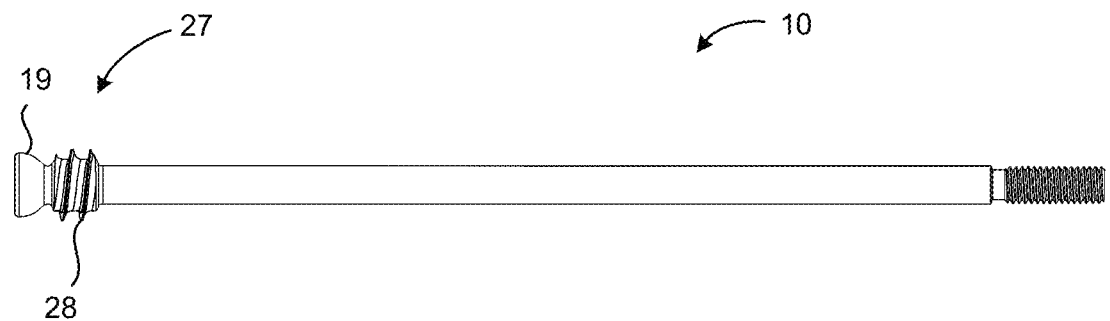
FIG. 6A illustrates a side view of a male member, according to another embodiment of the present disclosure.
Figure 6B:
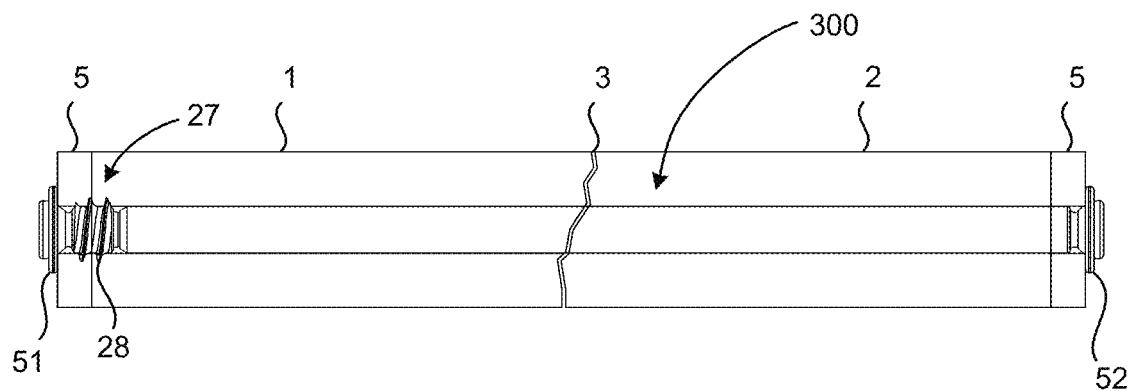
FIG. 6B illustrates a side view of a bone fixation assembly comprising the male member of FIG. 6A implanted in bone.
Figure 7A:
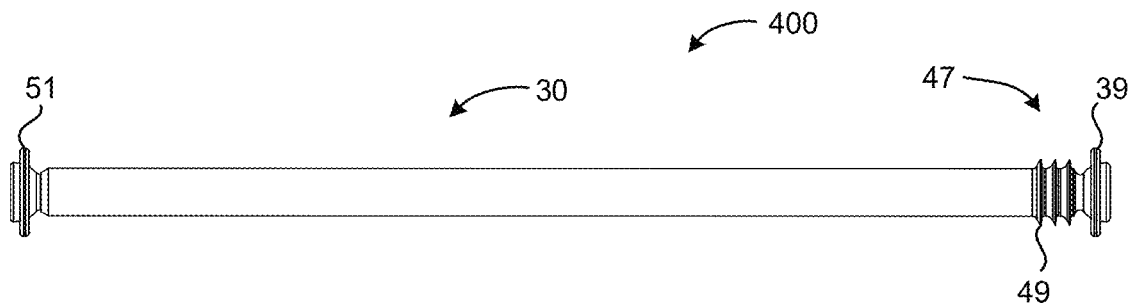
FIG. 7A illustrates a side view of a bone fixation assembly comprising a female member, according to another embodiment of the present disclosure.
Figure 7B:
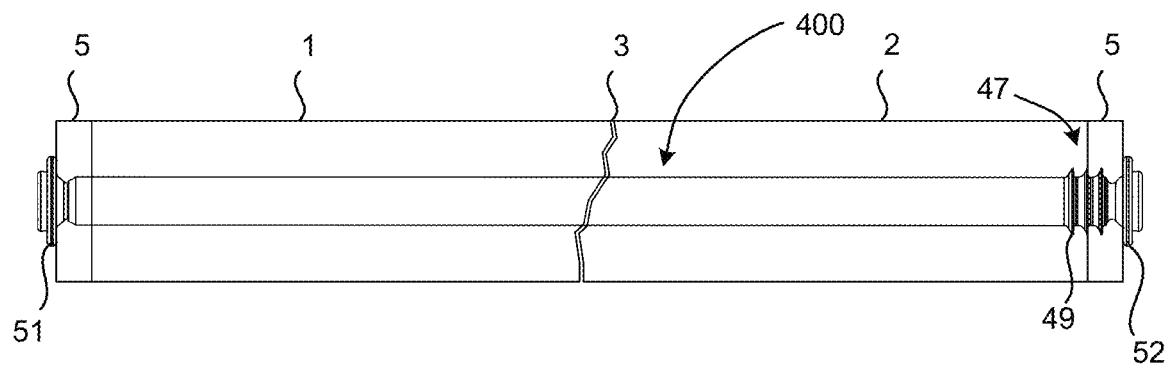
FIG. 7B illustrates a side view of the bone fixation assembly of FIG. 7A implanted in bone.
Figure 8A:
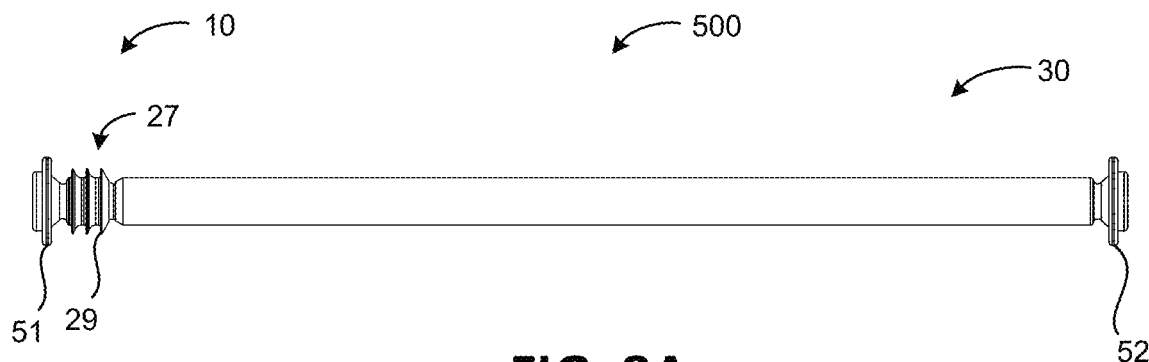
FIG. 8A illustrates a side view of a bone fixation assembly comprising a male member, according to another embodiment of the present disclosure.
Figure 8B:
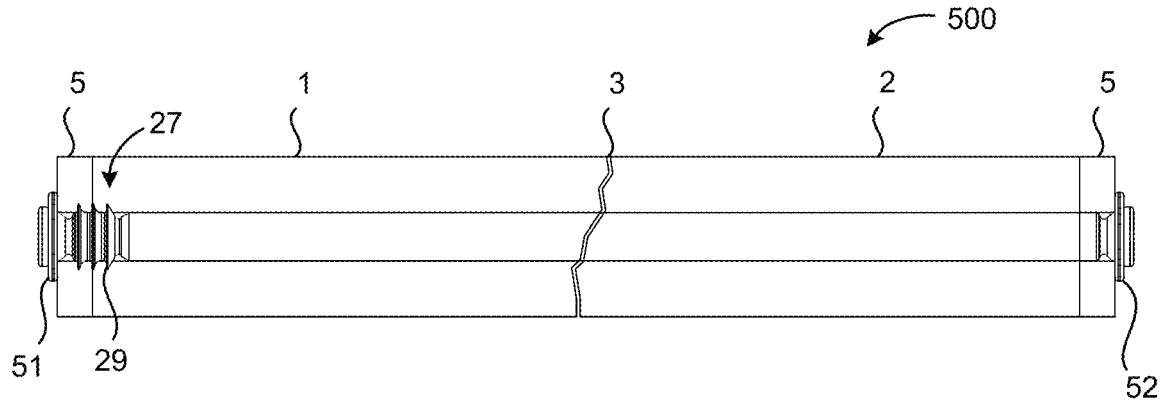
FIG. 8B illustrates a side view of the bone fixation assembly of FIG. 8A implanted in bone.
Figure 9A:
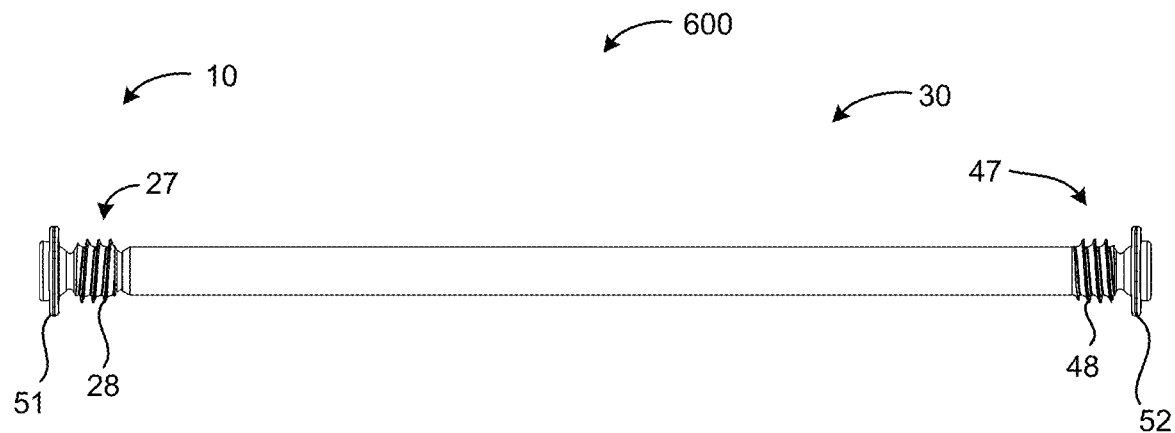
FIG. 9A illustrates a side view of a bone fixation assembly comprising a male member and a female member, according to another embodiment of the present disclosure.
Figure 9B:
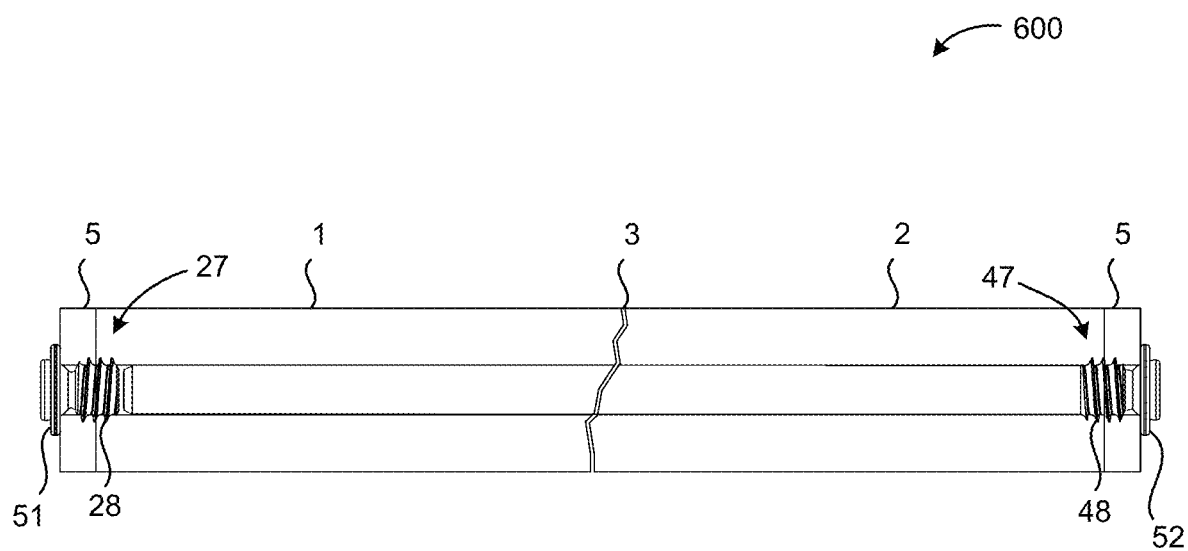
FIG. 9B illustrates a side view of the bone fixation assembly of FIG. 9A implanted in bone.

FIGS. 5A-9B illustrate various bone fixation assemblies and components that include one or more bone retention features, according to embodiments of the present disclosure. Specifically, FIG. 5A is a side view of a female member 30 including a second bone retention feature 47; FIG. 5B is a side view of a bone fixation assembly 200 comprising the female member 30 of FIG. 5A implanted in bone; FIG. 6A is a side view of a male member 10 including a first bone retention feature 27; FIG. 6B is a side view of a bone fixation assembly 300 comprising the male member 10 of FIG. 6A implanted in bone; FIG. 7A is a side view of a bone fixation assembly 400 comprising a female member 30 including a second bone retention feature 47; FIG. 7B is a side view of the bone fixation assembly 400 implanted in bone; FIG. 8A is a side view of a bone fixation assembly 500 comprising a male member 10 including a first bone retention feature 27; FIG. 8B illustrates a side view of the bone fixation assembly 500 implanted in bone; FIG. 9A is a side view of a bone fixation assembly 600 comprising a male member 10 and a female member 30 that include a first bone retention feature 27 and a second bone retention feature 47, respectively; and FIG. 9B is a side view of the bone fixation assembly 600 of FIG. 9A implanted in bone.

In some embodiments, the first bone retention feature 27 and the second bone retention feature 47 may be configured to respectively provide additional fixation for the male member 10 and the female member 30 within bone.

In some embodiments, the male member 10 may omit the male member head 19 and the first bone engaging feature 51, and/or the female member 30 may omit the female member head 39 and the second bone engaging feature 52. In these embodiments, the first bone retention feature 27 and/or the second bone retention feature 47 alone may provide sufficient fixation for the male member 10 and/or the female member 30 within bone (e.g., similar to a headless screw design).

In some embodiments, the male member head 19 may comprise the first bone retention feature 27, and/or the female member head 39 may comprise the second bone retention feature 47.

In some embodiments, the first bone retention feature 27 may include one or more first bone retention barbs 29 located adjacent the male member head 19, as shown in FIGS. 8A and 8B.

In some embodiments, the second bone retention feature 47 may include one or more second bone retention barbs 49 located adjacent the female member head 39, as shown in FIGS. 7A and 7B.

In some embodiments, a bone fixation assembly (not shown) may include one or more first bone retention barbs 29 formed on, or coupled with, the male member 10, as well as one or more second bone retention barbs 49 formed on, or coupled with, the female member 30.

In some embodiments, the one or more first bone retention barbs 29 and/or the one or more second bone retention barbs 49 may be oriented to resist axial movement in a proximal direction once the male member 10 and/or the female member 30 have been inserted into bone.

In some embodiments, the first bone retention feature 27 may include a first bone retention thread 28 having a first pitch. The first bone retention thread 28 may be located adjacent the male member head 19, as shown in FIGS. 6A, 6B, 9A, and 9B.

In some embodiments, the second bone retention feature 47 may include a second bone retention thread 48 having a second pitch. The second bone retention thread 48 may be located adjacent the female member head 39, as shown in FIGS. 5A, 5B, 9A, and 9B.

In some embodiments, the first bone retention thread 28 and/or the second bone retention thread 48 may resist axial movement in both a proximal direction and a distal direction once the first bone retention thread 28 and/or the second bone retention thread 48 have been inserted into bone.

In some embodiments, the first pitch of the first bone retention thread 28 may be equal to the second pitch of the second bone retention feature 47.

In some embodiments, the first pitch of the first bone retention thread 28 may be less than the second pitch of the second bone retention feature 47.

In some embodiments, the first pitch of the first bone retention thread 28 may be greater than the second pitch of the second bone retention feature 47.

In some embodiments, the first pitch of the first bone retention thread 28 and/or the second pitch of the second bone retention feature 47 may be equal to a third pitch of the external thread portion 20 and/or equal to a fourth pitch of the internal thread portion 40.

In some embodiments, the first pitch of the first bone retention thread 28 and/or the second pitch of the second bone retention feature 47 may be less than the third pitch of the external thread portion 20 and/or less than the fourth pitch of the internal thread portion 40.

In some embodiments, the first pitch of the first bone retention thread 28 and/or the second pitch of the second bone retention feature 47 may be greater than the third pitch of the external thread portion 20 and/or greater than the fourth pitch of the internal thread portion 40.

In some embodiments, some or all of the first bone retention thread 28, the second bone retention thread 48, the thread around the external thread portion 20, and/or the thread within the internal thread portion 40 may be right-hand threaded.

In some embodiments, some or all of the first bone retention thread 28, the second bone retention thread 48, the thread around the external thread portion 20, and/or the thread within the internal thread portion 40 may be left-hand threaded.

Referring now to FIGS. 10A-10G, example processes and methods for implanting bone fixation assemblies of the present disclosure into one or more bone portions are illustrated.

Figure 10A:
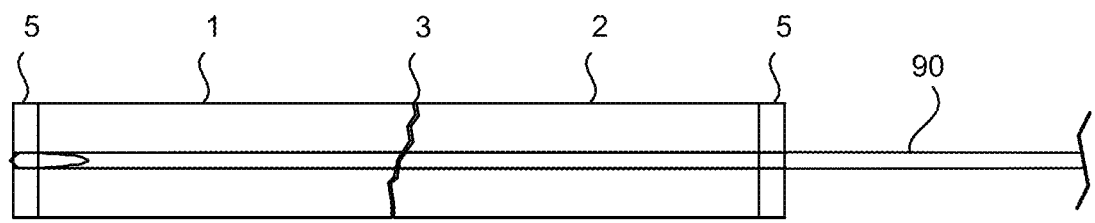
FIG. 10A illustrates a side view of a K-wire inserted into two portions of bone.
Figure 10B:
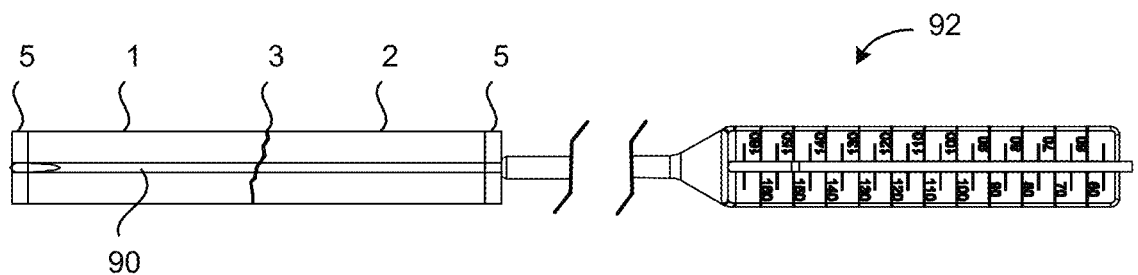
FIG. 10B illustrates a side view of a depth gauge inserted over the K-wire of FIG. 10A.

FIG. 10A illustrates insertion of a guidewire 90 (e.g., a K-wire, a Steinmann pin, etc.) through a first bone portion 1 and a second bone portion 2. Utilizing the guidewire 90 to guide insertion of the male member 10 and/or the female member 30 into the bone portions may enable percutaneous surgical procedures in lieu of open surgical procedures.

Once the guidewire 90 has been inserted through the first bone portion 1 and the second bone portion 2, a depth gauge 92 may be utilized to measure a length across the bone portions (e.g., see FIG. 10B) in order to determine a desired length for a suitable bone fixation assembly that may be implanted within the bone portions.

Figure 10C:
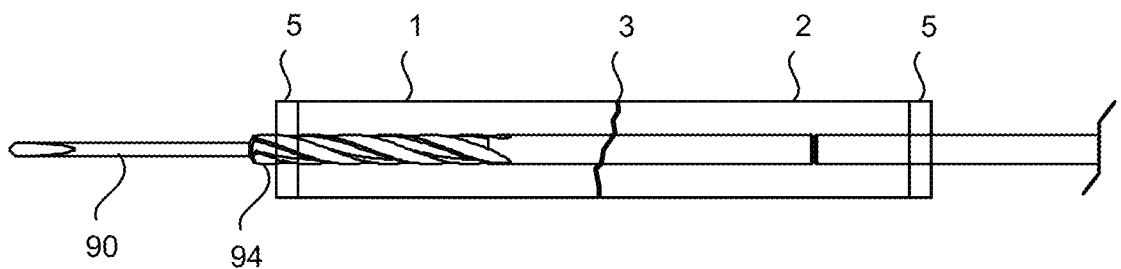
FIG. 10C illustrates a side view of a cannulated drill bit inserted into the two portions of bone of FIG. 10A.
Figure 10D:
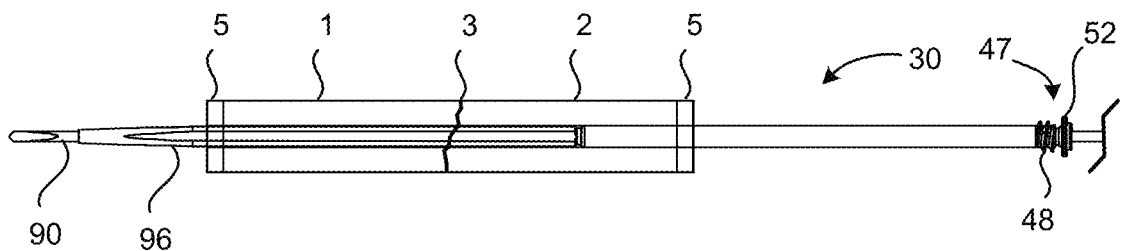
FIG. 10D illustrates a side view of an obturator inserted into the two portions of bone of FIG. 10A.

Once the length across the bone portions has been measured, a cannulated drill bit 94 may be inserted over the guidewire 90 to create a bone tunnel through the bone portions, as shown in FIG. 10C. In some embodiments, a diameter of the bone tunnel may be greater than or equal to an outer diameter of the female member 30.

Figure 10E:
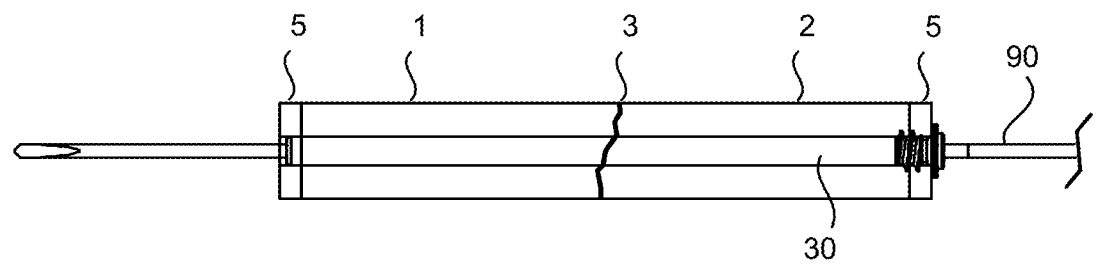
FIG. 10E illustrates a side view of the female member of FIG. 5A inserted into the two portions of bone of FIG. 10A.
Figure 10F:
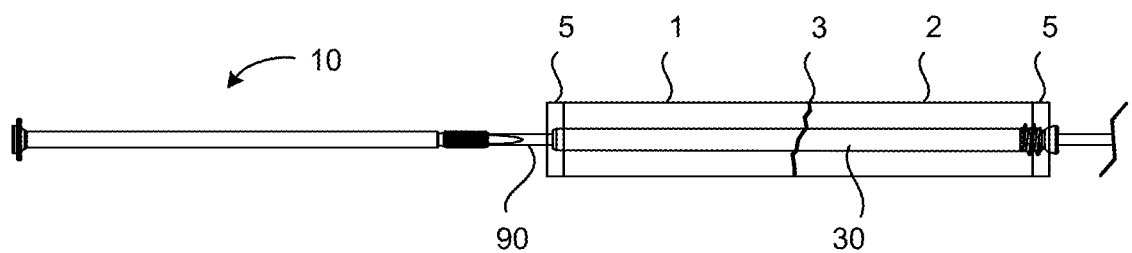
FIG. 10F illustrates a side view of the male member of FIG. 2A being guided into the female member of FIG. 10E.
Figure 10G:
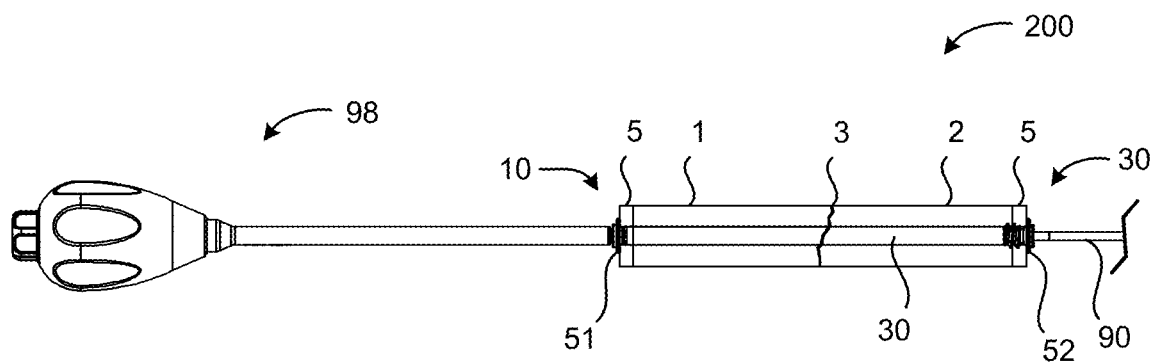
FIG. 10G illustrates a side view of the male and female members of FIG. 10F assembled together to form the bone fixation assembly of FIG. 5B implanted in the two portions of bone of FIG. 10A.

In some embodiments, once the bone tunnel has been formed an obturator 96 may be attached to the distal end 37 of the female member 30, and the assembled obturator 96 and female member 30 may be advanced over the guidewire 90 and into the bone tunnel. In some embodiments, the obturator 96 may help center the female member 30 within the bone tunnel so the female member 30 can more easily receive the male member 10 later in the surgical process. For female member 30 embodiments that comprise a second bone retention feature 47, a driver tool 98 (e.g., see FIG. 10G) may then be utilized to drive the second bone retention feature 47 into the bone, as shown in FIG. 10E. In some embodiments, the second bone retention feature 47 may comprise a left or right handed thread, as previously discussed herein. The male member 10 may then be inserted into the bone tunnel from an opposite direction and then coupled with the female member 30, as previously described. For example, FIG. 10G shows the male member 10 inserted into the bone tunnel, into the female member 30, and advanced with the driver tool 98 to rotate the right-hand thread on the external thread portion 20 to engage with the thread of the internal thread portion 40 and couple the male member 10 with the female member 30. Continued right-hand rotation of the male member 10 will cause the first bone engaging feature 51 to seat against the surface of the cortical bone region 5 to compress the disunion 3 and reduce the bone fracture. Moreover, in some embodiments, the second bone retention feature 47 of the female member 30 may comprise a second bone retention thread 48 that may be left-hand threaded. Accordingly, continued right-hand rotation of the male member 10 will also cause the second bone retention thread 48 of the female member 30 that is left-handed to provide additional purchase/fixation within the bone, such that advancement of the male member 10 into the female member 30 will not inadvertently push or rotate the female member 30 out of the bone.

Alternatively, or in addition thereto, a male member 10 may be inserted into the bone tunnel first (i.e., before the female member 30 has been inserted into the bone tunnel) by either placing the tip of the guidewire 90 into a blind bore 23 of the male member 10 (e.g., see FIG. 10F) and then advancing the male member 10 and guidewire 90 into the bone tunnel by pushing the guidewire 90 with the male member 10. In other embodiments, the guidewire 90 may be inserted through a male member through bore 24 or though bore and then the male member 10 may be advanced into the bone tunnel over the guidewire 90. Likewise, for male member 10 embodiments that comprise a first bone retention feature 27, a driver tool 98 may then be utilized to drive the first bone retention feature 27 into the bone. In some embodiments, the first bone retention feature 27 may comprise a left-hand thread, as previously discussed. In these embodiments, the female member 30 may then be inserted into the bone tunnel from an opposite direction and coupled with the male member 10 via right-hand rotation. Continued right-hand rotation of the female member 30 will cause the second bone engaging feature 52 to seat against the surface of the cortical bone region 5 to compress the disunion 3 and reduce the bone fracture. In these embodiments, continued right-hand rotation of the female member 30 will also cause the first bone retention thread 28 of the male member 10 that is left-handed to provide additional purchase/fixation within the bone, such that advancement of the female member 30 over the male member 10 will not inadvertently push or rotate the male member 10 out of the bone.

As previously discussed, FIGS. 9A and 9B illustrate a bone fixation assembly 600 that includes bone retention features on both the male member 10 and the female member 30. In this embodiment, the first bone retention feature 27 on the male member 10 may be left-hand threaded, and the second bone retention feature 47 on the female member 30 may be right hand-threaded, both having a first pitch. The threads on the external thread portion 20 and the internal thread portion 40 may be right-handed and have a second pitch. However, it will be also understood that, in other embodiments, the first bone retention feature 27 on the male member 10 may be right-hand threaded, the second bone retention feature 47 on the female member 30 may be left hand-threaded, and the threads on the external thread portion 20 and the internal thread portion 40 may be left-hand threaded.

In some embodiments, an installation technique for the bone fixation assembly 600 may begin with insertion of the male member 10 into a bone tunnel formed in the bone. Left-hand rotation of the male member 10 may then be used to seat the first bone engaging feature 51 (or male member head 19) against the cortex. Then, the female member 30 may be introduced into the bone tunnel from an opposite direction and engaged with the male member 10 via right-hand rotation of the female member 30. Further right-hand rotation of the female member 30 relative to the male member 10 will cause the second bone retention feature 47 to thread into the bone. It will be appreciated that if the first pitch and the second pitch are the same, then there will be no change in the relative positions between the two bone portions during the assembly process, thus effecting a positional screw technique. However, if the first pitch is less than the second pitch, then the two bone portions will be drawn together during the assembly process, thus effecting a compression screw technique.

Any processes, procedures, or methods disclosed herein may comprise one or more steps or actions for performing a described process, procedure, or method. Each of the process, procedure, or method steps and/or actions may be interchanged with one another. In other words, unless a specific order of steps or actions is required for proper operation of a described embodiment, the inclusion/use of specific steps and/or actions, as well are their order, may be modified in any manner.

Figure 11A:
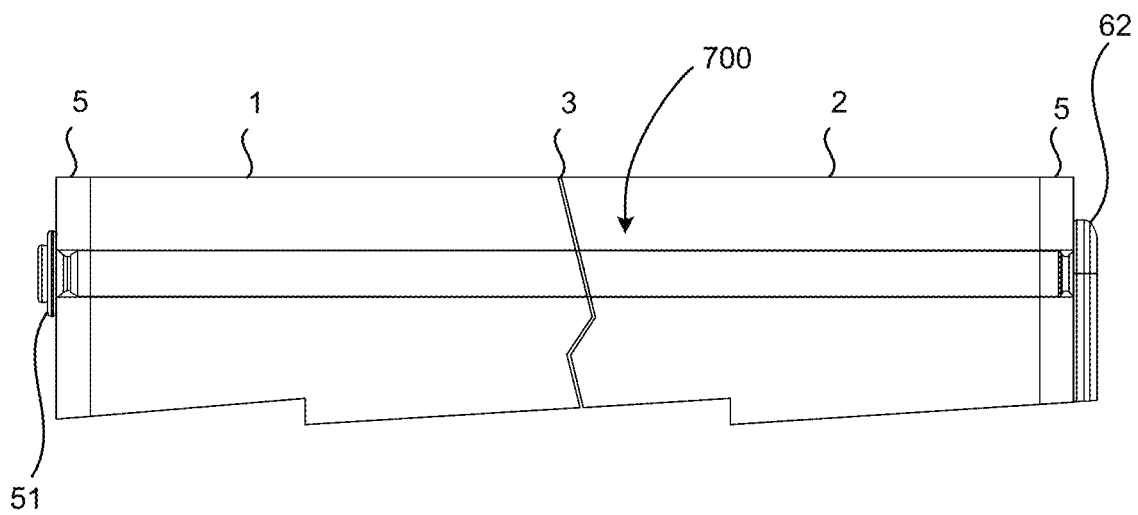
FIG. 11A illustrates a side view of a bone fixation assembly, according to another embodiment of the present disclosure.
Figure 11B:
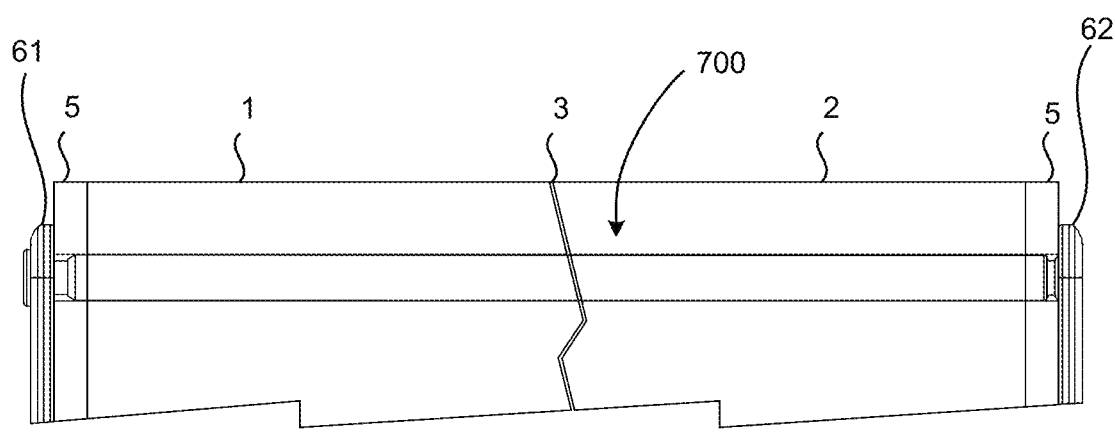
FIG. 11B illustrates a side view of a bone fixation assembly, according to another embodiment of the present disclosure.
Figure 12A:
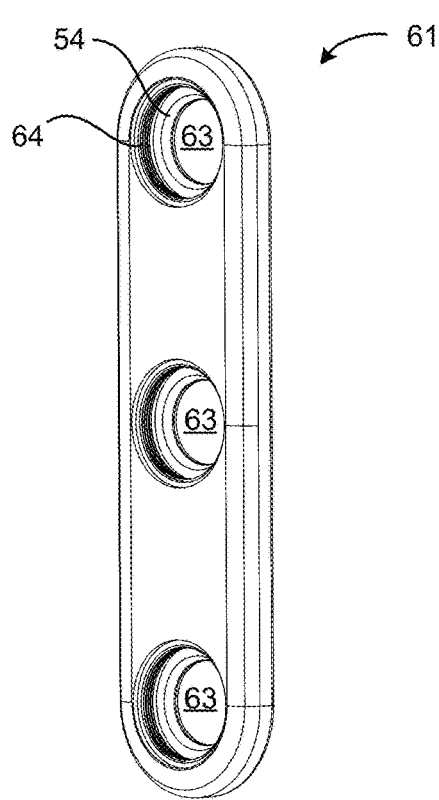
FIG. 12A illustrates a perspective top view of a bone plate, according to an embodiment of the present disclosure.
Figure 12B:
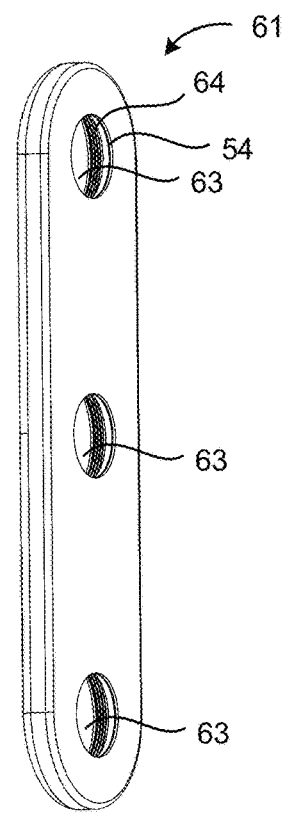
FIG. 12B illustrates a perspective bottom view of the bone plate of FIG. 12A.

FIGS. 11A-12B illustrate views of a bone fixation assembly 700 an its components comprising a first bone plate 61 and/or a second bone plate 62, according to some embodiments of the present disclosure. FIG. 11A is a side view of the bone fixation assembly 700 including a first bone engaging feature 51 comprising a washer and a second bone engaging feature comprising a second bone plate 62. FIG. 11B illustrates a side view of the bone fixation assembly 700 including a first bone plate 61 and a second bone plate 62. In these embodiments, the male member 10 and the female member 30 may be inserted through one or more bone plate apertures 63 that may be formed through the first bone plate 61 and/or the second bone plate 62. The male member head 19 of the male member 10 and/or the female member head 39 of the female member 30 may engage surfaces on the first bone plate 61 and/or the second bone plate 62 to hold and/or compress the first bone plate 61 and the second bone plate 62 against the bone portions.

In some embodiments, the first partially spherical surfaces 53 of the male member head 19 and the female member head 39 may respectively engage with second partially spherical surfaces 54 that encircle the one or more bone plate apertures 63 (e.g., see FIGS. 12A and 12B) in order to hold and/or compress the first bone plate 61 and the second bone plate 62 against the bone portions, as well as allow for polyaxial fixation of the bone plates with respect to the male member head 19 and the female member head 39.

Figure 13A:
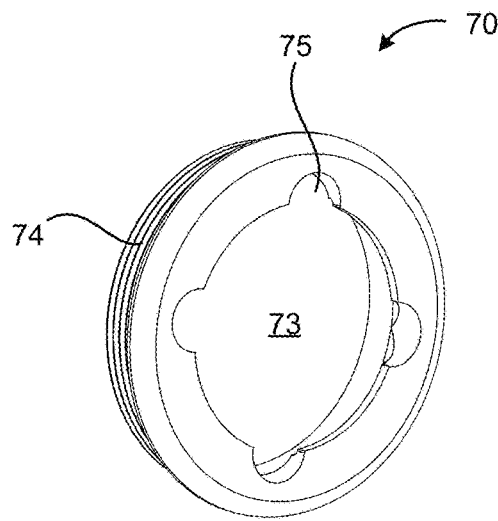
FIG. 13A illustrates a perspective top view of a retention cap, according to an embodiment of the present disclosure.
Figure 13B:
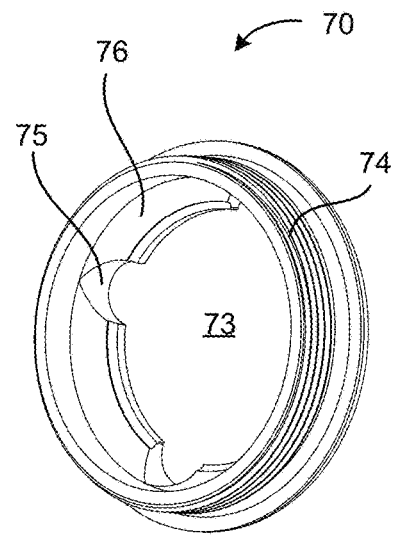
FIG. 13B illustrates a perspective bottom view of the retention cap of FIG. 13A.
Figure 14A:
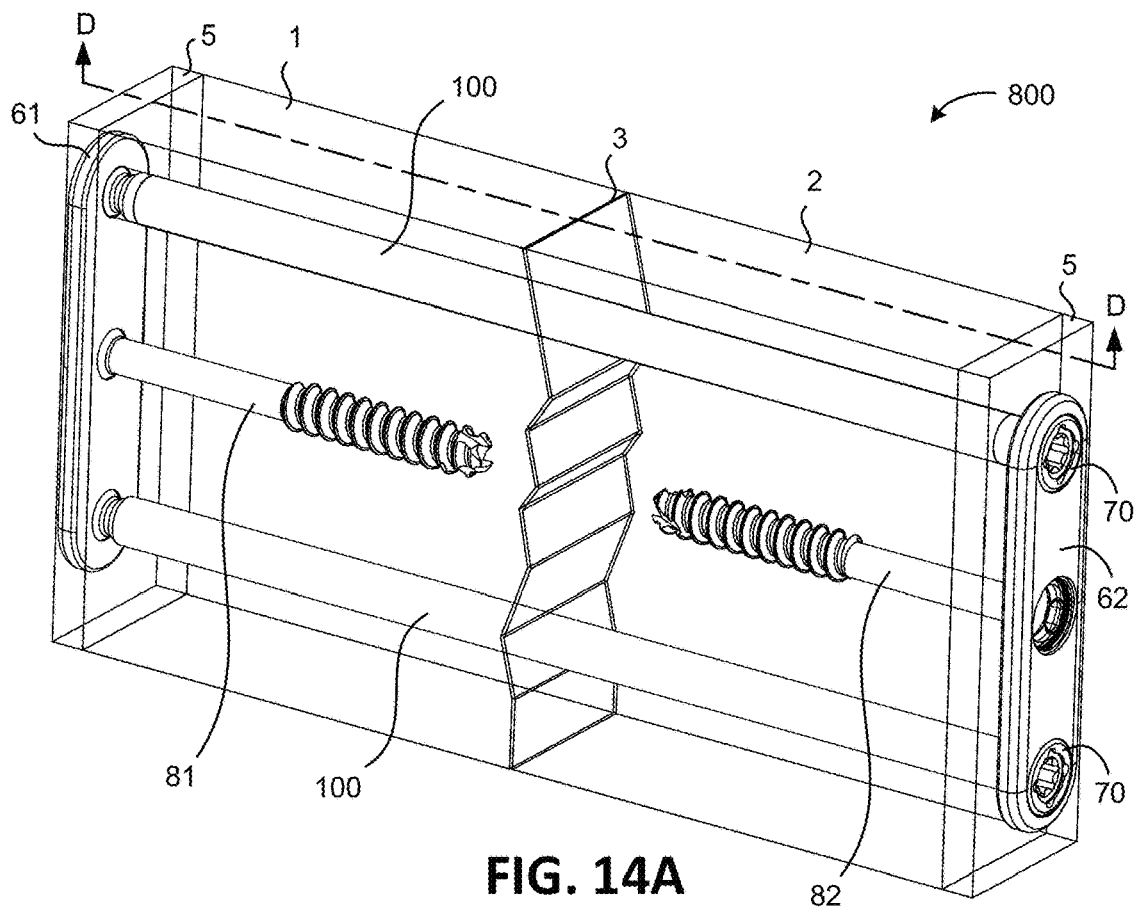
FIG. 14A illustrates a perspective view of a bone fixation assembly implanted in bone, according to another embodiment of the present disclosure.
Figure 14B:
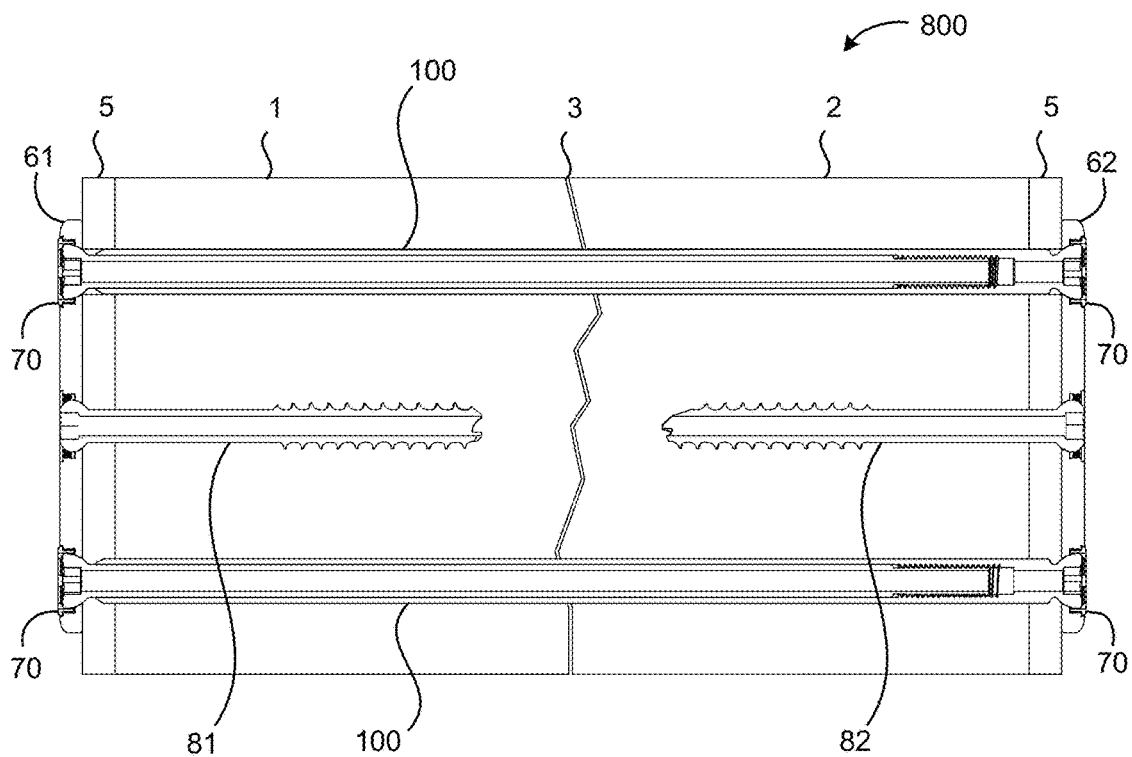
FIG. 14B illustrates a cross-sectional side view of the bone fixation assembly of FIG. 14A taken along the line D-D in FIG. 14A.

FIGS. 12A-14B illustrate various views of a bone fixation assembly 800 an its components comprising a first bone plate 61, a second bone plate 62, a first bone screw 81, a second bone screw 82, and one or more retention caps 70, according to another embodiment of the present disclosure. FIG. 14A is a perspective view of the bone fixation assembly 800 implanted in bone and FIG. 14B is a cross-sectional side view of the bone fixation assembly 800 taken along the line D-D in FIG. 14A.

In some embodiments, the first bone screw 81 and/or the second bone screw 82 may couple the first bone plate 61 and/or the second bone plate 62 to the bone portions.

In some embodiments, the one or more retention caps 70 shown in FIGS. 13A and 13B may include a retention cap aperture 73, a retention cap thread 74, one or more retention cap drive features 75, and one or more retention surfaces 76.

In some embodiments, the one or more retention caps 70 may be coupled with the first bone plate 61 and/or the second bone plate 62 before the bone fixation assemblies and bone plates have been adjusted to a desired position.

In some embodiments, the one or more retention caps 70 may be coupled with the first bone plate 61 and/or the second bone plate 62 after the bone fixation assemblies and bone plates have been secured to the bone and/or adjusted to a desired position.

In some embodiments, the retention cap thread 74 may be configured to removably couple with the bone plate thread 64 encircling the one or more bone plate apertures 63. The one or more surfaces 76 of the retention cap 70 may be configured to engage with at least one of the male member head 19 and/or the female member head 39 as the male member 10 and/or or female member 30 are rotated with respect to each other to increase an overall length of the bone fixation assembly 800. Likewise, the second partially spherical surfaces 54 of the bone plates may be configured to engage with at least one of the male member head 19 and/or the female member head 39 as the male member 10 and/or or female member 30 are rotated with respect to each other to decrease an overall length of the bone fixation assembly 800. In this manner, a surgeon may precisely control a spacing between the bone plates via relative rotation of the male member 10 with respect to the female member 30 in either direction.

In some embodiments, the one or more retention caps 70 may also be configured to prevent movement of the male member head 19 and/or the female member head 39 relative to the bone plates by sufficiently tightening the one or more retention caps 70 to forcefully trap the male member head 19 and/or the female member head 39 between the one or more surfaces 76 of the retention cap 70 and the second partially spherical surfaces 54 of the bone plate. In this manner, the male member head 19 and/or the female member head 39 may be selectively retained to the first bone plate 61 and/or the second bone plate 62 with the one or more retention caps 70 in order to preserve a desired spacing between the bone plates, prevent further movement of the male member 10 and/or the female member 30 with respect to the bone plates, and/or as an anti-back out feature for the member head 19 and/or the female member head 39.

In some embodiments, a driver tool (not shown) may include one or more driver features configured to engage the one or more retention cap drive features 75 in order to removably couple and decouple the one or more retention caps 70 from the first bone plate 61 and the second bone plate 62.

However, it will also be understood that other connection means (instead of threads) may be utilized to couple the one or more retention caps 70 to the bone plates including, but not limited to: snap rings, retaining rings, press fits, etc.

In some embodiments, right-hand relative rotation between the male member 10 and the female member 30 may draw the bone plates together, and left-hand relative rotation between the male member 10 and the female member 30 may push the bone plates apart.

In some embodiments, left-hand relative rotation between the male member 10 and the female member 30 may draw the bone plates together, and right-hand relative rotation between the male member 10 and the female member 30 may push the bone plates apart.

In this manner, a surgeon has the ability to precisely control the spacing/position between the first bone plate 61 and the second bone plate 62 coupled to the bone portions via the first bone screw 81 and the second bone screw 82. Once a desired spacing/position between the first bone plate 61 and the second bone plate 62 has been achieved, the selected spacing/position between the bone plates may be maintained during the healing process (or further adjusted, as desired). Thus, the bone fixation assembly 800 may be utilized for more complicated bone fractures with many bone fragments (e.g., comminuted fractures), where precision control of bone plate spacing can ensure that an outer envelope of a bone is held in an anatomically correct position during the healing process while the bone fixation assembly 800 resists potential collapse within a zone of comminution.

Figure 15:
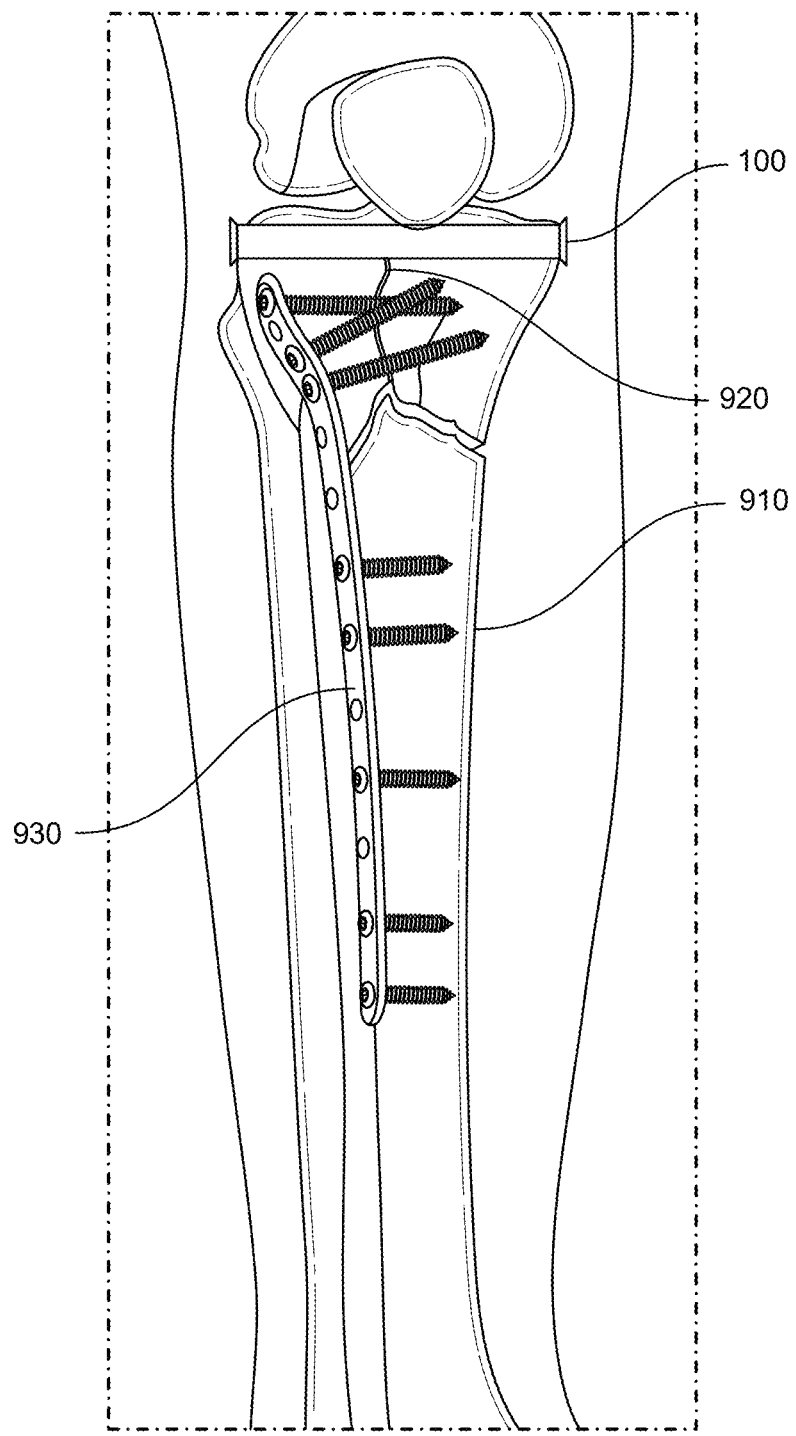
FIG. 15 illustrates an anterior view of a tibia with the bone fixation assembly of FIG. 4A stabilizing a proximal tibial fracture.
Figure 16:
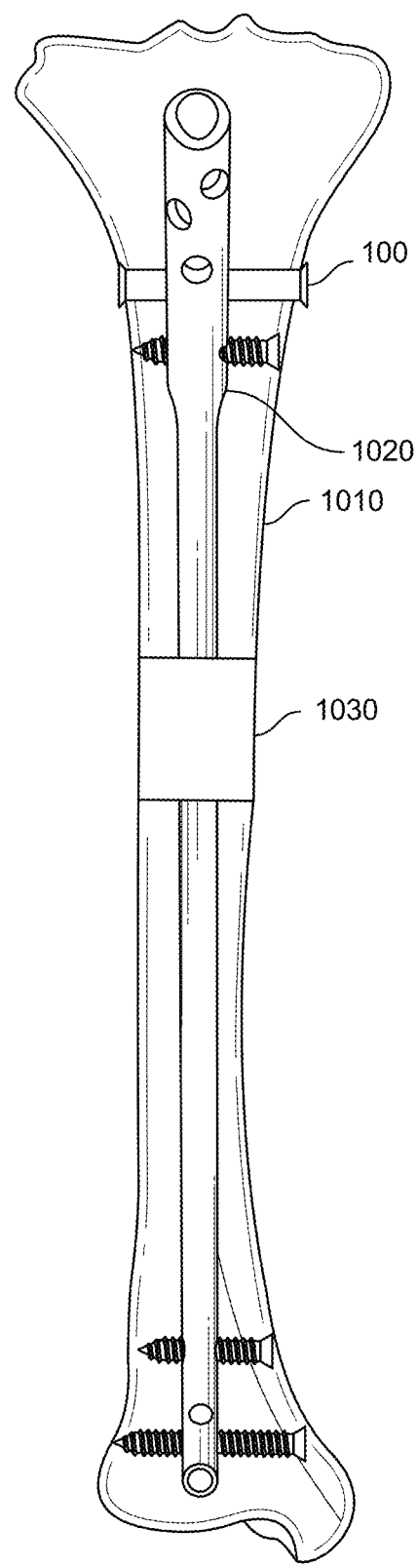
FIG. 16 illustrates an anterior view of a tibia with the bone fixation assembly of FIG. 4A stabilizing an intramedullary nail.

FIGS. 15 and 16 illustrate two example surgical procedures utilizing bone fixation assemblies of the present disclosure. However, it will also be understood that the bone fixation assemblies of the present disclosure may be utilized in any number of different surgical procedures that may or may not be described or contemplated herein. FIG. 15 illustrates an anterior view of a tibia 910 with a tibial bone plate 930 and a bone fixation assembly 100 implanted in a proximal end of the tibia 910 to stabilize a proximal tibial fracture 920. FIG. 16 illustrates an anterior view of a tibia 1010 with an intramedullary nail 1020 implanted within an intramedullary canal of the tibia 1010 to stabilize a midshaft tibial fracture 1030. A bone fixation assembly 100 is also inserted through an aperture formed through the intramedullary nail 1020 to provide cross fixation of the intramedullary nail 1020 and stabilize/hold the intramedullary nail 1020 within the intramedullary canal during the healing process.

Figure 17A:
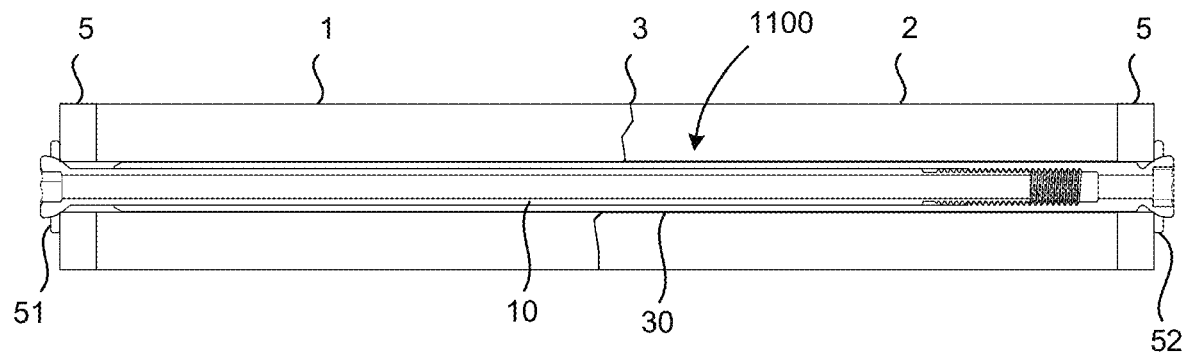
FIG. 17A illustrates a side view of a bone fixation assembly implanted in bone and positioned in a first configuration, according to another embodiment of the present disclosure.
Figure 17B:
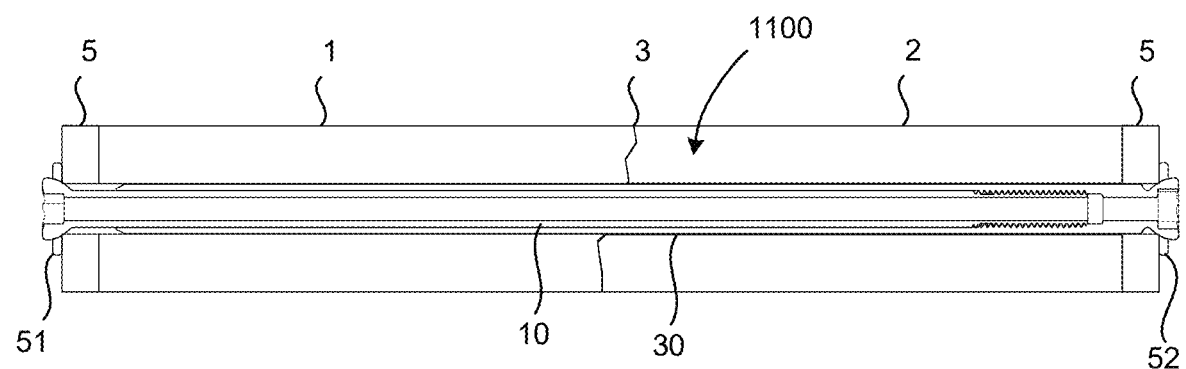
FIG. 17B illustrates a side view of the bone fixation assembly of FIG. 17A positioned in a second configuration.
Figure 17C:
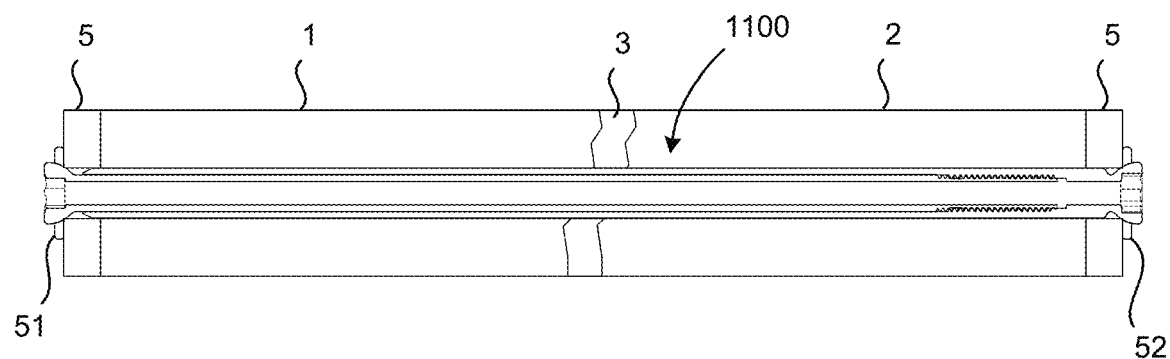
FIG. 17C illustrates a side view of the bone fixation assembly of FIG. 17A positioned in a third configuration.

FIGS. 17A-17C illustrate various cross-sectional views of a bone fixation assembly 1100 implanted in bone that comprises a low tensile modulus material, according to another embodiment of the present disclosure. Specifically, FIG. 17A is a cross-sectional side view of the bone fixation assembly 1100 positioned in a first configuration; FIG. 17B illustrates a cross-sectional side view of the bone fixation assembly 1100 positioned in a second configuration; and FIG. 17C illustrates a cross-sectional side view of the bone fixation assembly 1100 positioned in a third configuration.

As used herein, the phrase "low tensile modulus material" includes any material that may stretch to a surgically relevant amount under loads/strains applied to a material that are below a tensile yield point of the material.

In some embodiments, the first configuration may comprise a non-stretched state of the low tensile modulus material, the second configuration may comprise a fully stretched state of the low tensile modulus material, and the third configuration may comprise a partially stretched state of the low tensile modulus material.

In some embodiments, at least a portion of the male member 10 and/or at least a portion of the female member 30 may comprise one or more low tensile modulus materials.

A common measurement for stretch is strain, which may be expressed as a percentage. Strain may be defined as the ratio of the increase in overall length of a material in a stretched state divided by the overall length of the material in an un-stretched state.

Illustrative examples of strain values for some commonly used implant materials that may be stressed just below the material's tensile yield stress may include, but are not limited to: Stainless steel alloys-0.3 to 0.7%; Alpha-beta titanium alloys—0.8% to 1.0%; Beta titanium alloys 1.0% to 1.2%; 30% carbon fiber filled polyetheretherketone (PEEK)—1.9% to 2.0%; Natural PEEK-2.7% to 2.9%; Super-elastic nickel-titanium alloys (nitinol)—8% to 12%;

In some embodiments, 1% of stretch/strain may yield 0.25 mm to 1.0 mm of elastic recovery for 25 mm and 100 mm stretchable length bone fixation assemblies, respectively.

In some embodiments, 2% to 3% of stretch/strain may yield 0.50 mm to 0.75 mm and 2.0 mm to 3.0 mm of elastic recovery for 25 mm and 100 mm stretchable length bone fixation assemblies, respectively.

In some embodiments, 8% to 12% of stretch/strain may yield 2.0 mm to 3.0 mm and 8.0 mm to 12.0 mm of elastic recovery for 25 mm and 100 mm stretchable length bone fixation assemblies, respectively.

In this manner, bone fixation assemblies that include an elastic recovery length may provide maintenance of compression across the fracture surface or disunion 3 of two or more bone portions as the bone contracts under load due to its viscoelastic properties, or as the bone remodels or shifts during the healing period. Without maintenance of compression across the fracture surface or disunion 3 of the two bone portions, a gap may develop at the fracture surface or disunion 3, which may impede the development of bridging bone across the fracture surface or disunion 3, which may result in non-union or mal-union of the two or more bone portions.

FIG. 17A shows the bone fixation assembly 1100 in a fully seated position securing the two bone portions in direct apposition.

FIG. 17B shows the bone fixation assembly 1100 of FIG. 17A after continued relative right-hand rotation of the male member 10 with respect to the female member 30. This may increase the compressive force at the fracture surface or disunion 3 and increase the tensile stresses in the male member 10 and/or female member 30 that may comprise the low tensile modulus material. These increasing tensile stress may cause the bone fixation assembly 1100 to stretch elastically to an overall length that may be greater than the overall length of the bone fixation assembly 1100 shown in FIG. 17A. In some embodiments, a driver tool comprising a torque measurement feature (not shown) may be utilized to select and/or adjust a compression force placed on the bone portions by the bone fixation assembly 1100. Moreover, a disposable breakaway torque wrench or driver tool (not shown) may be provided in a kit with any of the bone fixation assemblies or any components of the bone fixation assemblies described herein.

FIG. 17C shows the bone fixation assembly 1100 of FIG. 17B after the bone has contracted due to its viscoelastic properties (or due to shifting, bone remodeling, etc.), causing the opposed cortices of the two bone portions to move closer together. The bone fixation assembly 1100 may also shorten due to partial recovery of its elastic stretch, thereby maintaining compression across the fracture surface or disunion 3.

Moreover, in some embodiments additional resilient structures may be added to the bone fixation assemblies described herein in order to achieve additional bone compression during the healing process including, but not limited to: compression washers, springs, resilient members, etc.

Experiment 1: Three-Point Bending Load Test

In this experiment, finite element models were created for: (1) a prior art, partially-threaded, cannulated screw (not shown) having an outer thread diameter of 7.0 mm and an overall length of 160 mm; and (2) a bone fixation assembly according to the present disclosure with an outer diameter of 7.0 mm and an overall length of 160 mm. Bending loads of the same magnitude were applied to midpoints of both finite element models with the ends of each model supported in order to create a three-point bend loading condition in each model. Finite element analyses were then performed to determine a maximum Von Mises stress and a maximum displacement for each model. From these data, a relative strength and a relative stiffness ratio for each model was computed. The strength and the stiffness of the cannulated screw model was used as the denominator for the ratios. Thus, the relative strength and relative stiffness of the cannulated screw is 1.0.

Figure 18:
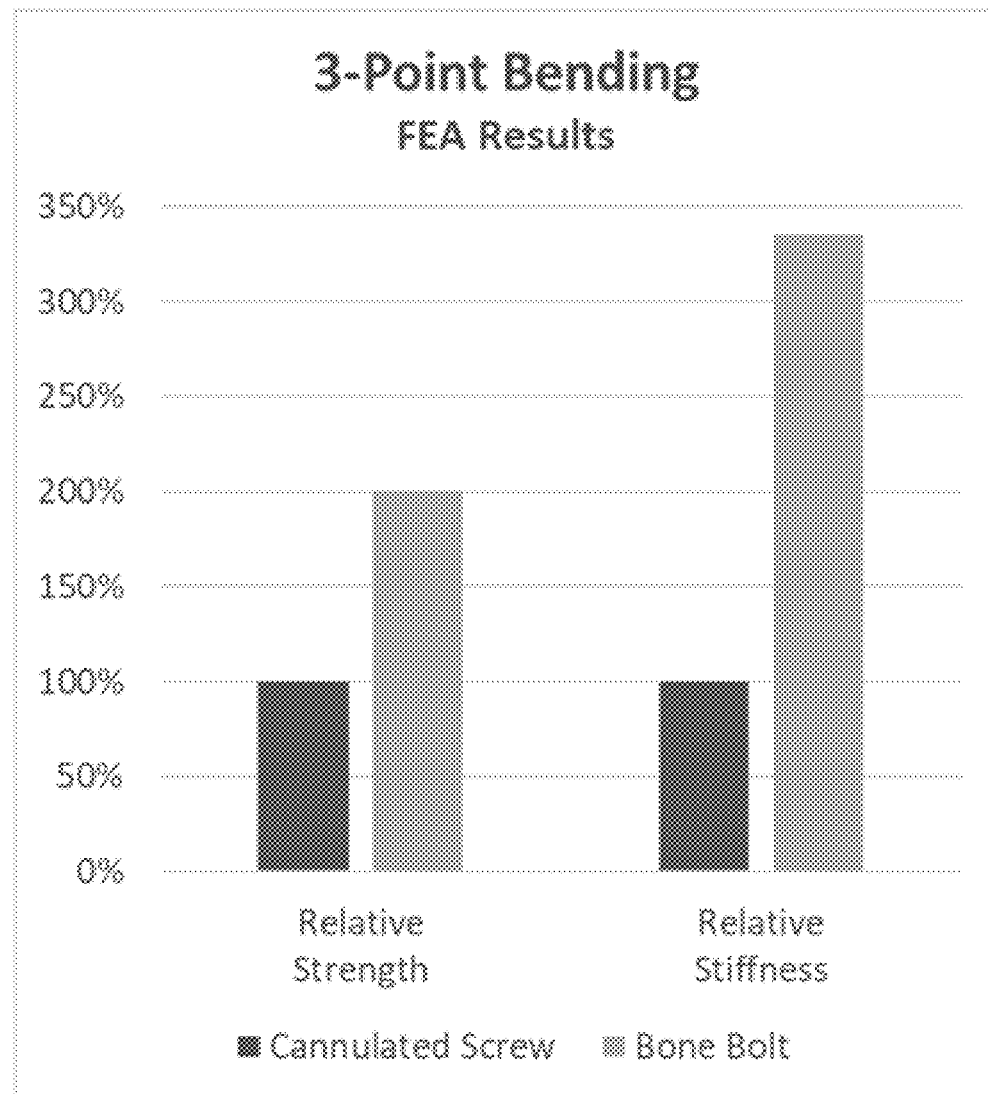
FIG. 18 is a chart illustrating relative strength and stiffness results in a 3-point bending experiment.

FIG. 18 is a chart depicting the relative strength and relative stiffness of the bone fixation assembly model vs. the cannulated screw model based on the finite element analyses of the three-point bending test. Thus, FIG. 18 demonstrates that the bone fixation assembly model has twice the strength and over three times the stiffness of the cannulated screw under three-point bending load conditions. Accordingly, the bone fixation assemblies of the present disclosure will provide a much stronger, stiffer, and more stable bone repair construct than prior art devices, such as cannulated bone screws, thereby reducing the risk of implant loosening, implant failure, and/or loss of compression at a fracture surface or disunion 3.

Experiment 2: Four-Point Bending Load Test

In this experiment, the same finite element models described in Experiment 1 were utilized. Bending loads of the same magnitude were applied at the one third and two third locations of the overall length of the model with the ends of the model supported to create a four-point bend loading condition in each model. Finite element analyses were then performed to determine a maximum Von Mises stress and a maximum displacement for each model. From these data, a relative strength and a relative stiffness ratio for each model was computed. The strength and the stiffness of the cannulated screw model was used as the denominator for the ratios. Thus, the relative strength and relative stiffness of the cannulated screw is 1.0.

Figure 19:
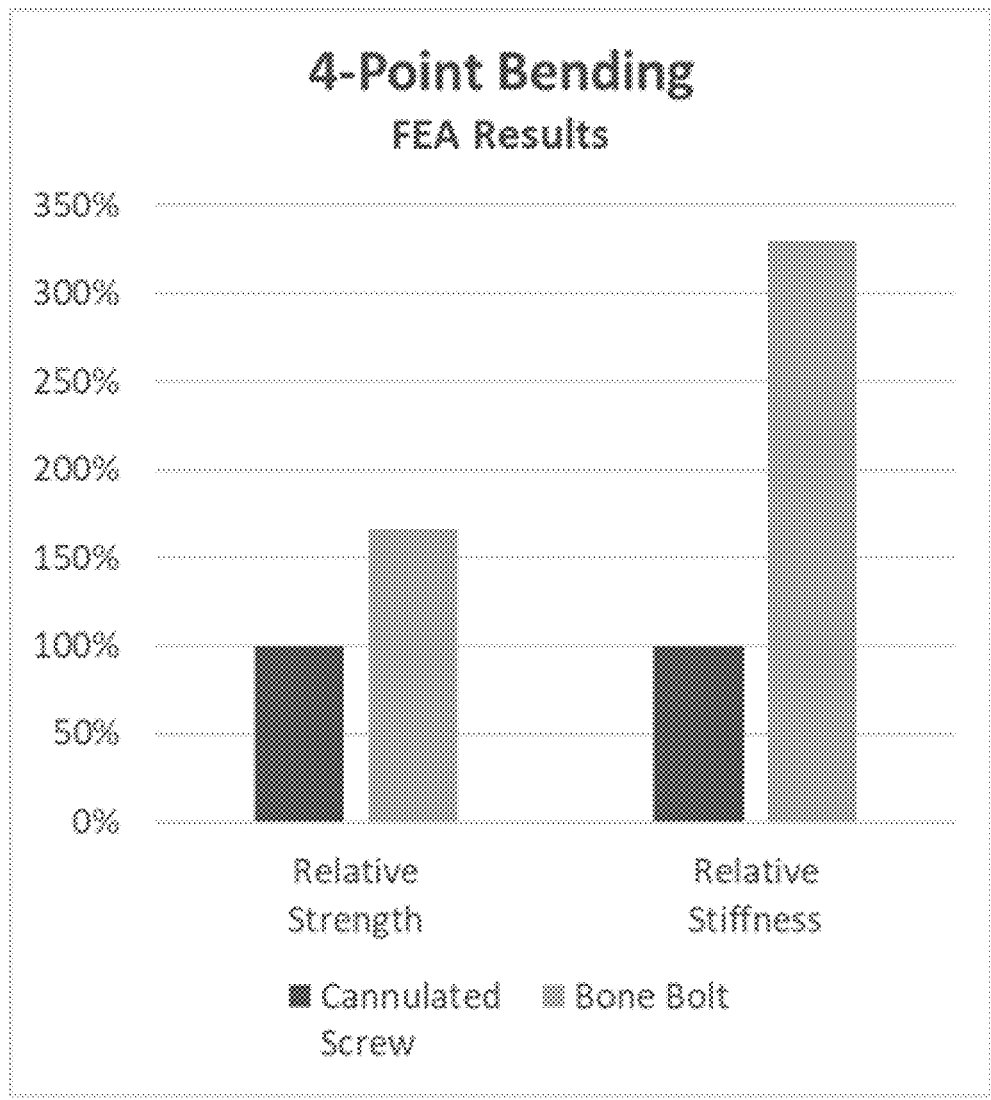
FIG. 19 is a chart illustrating relative strength and stiffness results in a 4-point bending experiment.

FIG. 19 is a chart depicting the relative strength and relative stiffness of the bone fixation assembly model vs. the cannulated screw model based on the finite element analyses of the four-point bending test. Thus, FIG. 19 demonstrates that the bone fixation assembly model has over 1.5 times the strength and over three times the stiffness of the cannulated screw under a four-point bending load condition. Accordingly, the bone fixation assemblies of the present disclosure will provide a much stronger, stiffer, and more stable bone repair construct than prior art devices, such as cannulated bone screws, thereby reducing the risk of implant loosening, implant failure, and/or loss of compression at a fracture surface or disunion 3.

Experiment 3: Pull-Out Strength Test

In this experiment, calculations were performed to determine the force required to pull one end of the device out of a bone into which it is fixed. Pull-out force was calculated for two devices: (1) a partially-threaded, cannulated screw having an outer thread diameter of 7.0 mm, an inner thread diameter of 5.2 mm, and a pitch of 2.0 mm; and (2) a bone fixation assembly according to the present disclosure with an outer diameter of 7.0 mm, a head diameter of 8.5 mm, and a washer having an outer diameter of 12.7 mm. For both of these devices, it was assumed that each device was fixed in 3 mm of cortical bone having a shear strength of 50 megapascals (MPa). A pull-out force for the cannulated screw was calculated using an empirical formula developed to determine screw pull-out force from bone (Chapman, J R, et al. Factors Affecting the Pullout Strength of Cancellous Bone Screws. Journal of Biomechanical Engineering. 1996.). This reference is incorporated by reference herein in its entirety. A pull-out force for the bone fixation assembly was then calculated using the constitutive equation for shear stress. From these calculated results a relative pull-out strength was computed and the strength of the cannulated screw was used as the denominator for the ratio. Thus, the relative strength of the cannulated screw is 1.0.

Figure 20:
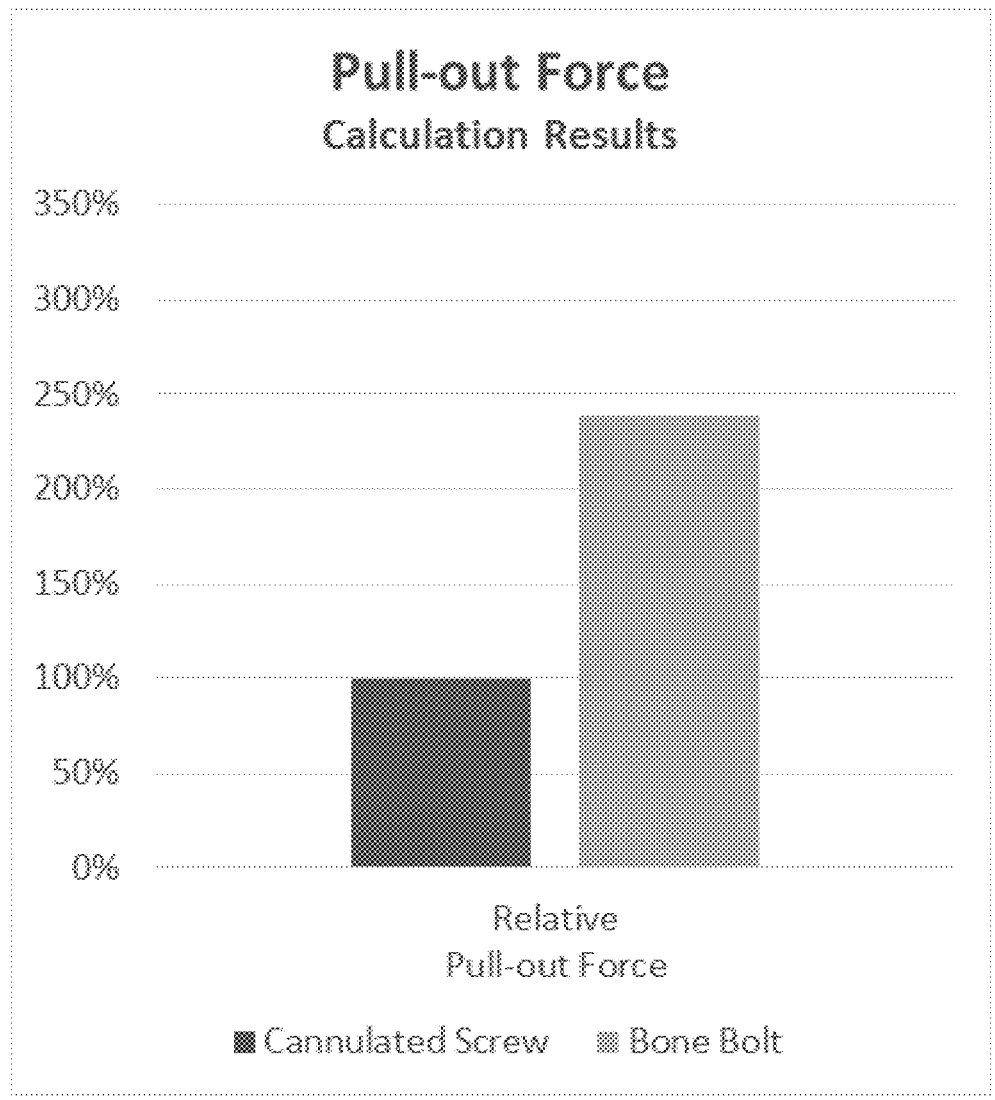
FIG. 20 is a chart illustrating relative pull-out force results in a pull-out force experiment.

FIG. 20 is a chart depicting the relative pull-out force of the bone fixation assembly vs. the cannulated screw based on calculations of constitutive and empirical equations. Thus, FIG. 20 demonstrates that the bone fixation assembly has over twice the pull-out strength of the cannulated screw. As pull-out strength directly relates to implant loosening in the post-operative healing period following a bone repair surgical procedure, bone fixation assemblies of the present disclosure will reduce the risk of implant loosening which can lead to a reoperation rate of 11.8% for patients that are surgically treated for pelvic ring injury.

FIG. 21 illustrates a table that includes some example dimensions which may be utilized with the bone fixation assemblies of present disclosure. The table is entitled "Table 1: Example Bone Fixation Assembly Dimensions." Table 1 of FIG. 21 also lists some example dimensions for comparably sized bone screws. However, it will be understood that the example dimensions listed in Table 1 are non-limiting examples only, and any dimensions may be utilized with the bone fixation assemblies of present disclosure.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

As used herein, the term "proximal" means a location at the end of a part that faces a user when the user is installing the part. The term "distal" means a location at the opposite end of the proximal end. For example, when a user installs a bone screw into a material with a driver, the end of the bone screw engaged with the driver is the proximal end, and the tip of the bone screw that first engages the material is the distal end. The term "cannulated" means having a central bore extending along a longitudinal axis of a part between a proximal end and a distal end of the part.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. As defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A bone fixation assembly comprising:
   a male member, the male member comprising:
   a male member shaft comprising:
   a proximal end;
   a distal end; and
   a first longitudinal axis;
   a first bone engaging feature at the proximal end of the male member shaft;
   an external thread portion at the distal end of the male member shaft, the external thread portion having a first length and a first major diameter; and
   a male load-sharing feature intermediate the first bone engaging feature and the external thread portion, the male load-sharing feature having a second length and an outer diameter defining at least one male load-sharing surface; and a female member, the female member comprising:
  a female member shaft comprising:
    a proximal end;
    a distal end; and
    a second longitudinal axis;
  a second bone engaging feature at the proximal end of the female member shaft;
  an internal thread portion having a third length and a second major diameter, the internal thread portion configured to receive the external thread portion of the male member to removably couple the male member with the female member; and
  a female load-sharing feature located distal to the internal thread portion and extending between the internal thread portion and the distal end of the female member shaft, the female load-sharing feature having a fourth length and an inner diameter defining at least one female load-sharing surface, the female load-sharing feature positioned and shaped to receive the male load-sharing feature therein;
  the inner diameter is slightly greater than the outer diameter to create a very close sliding fit between the female load-sharing feature and the male load-sharing feature.

2. The bone fixation assembly of claim 1, wherein at least one of the at least one male load-sharing surface and the at least one female load-sharing surface comprises a cylindrical surface.

3. The bone fixation assembly of claim 1, wherein the male load-sharing feature is configured to slide and rotate within the female load-sharing feature during assembly of the male member to the female member.

4. The bone fixation assembly of claim 1, wherein at least one of the male member and the female member comprise a low tensile modulus material that is configured to provide a compression force to the bone.

5. The bone fixation assembly of claim 1, wherein the male member comprises one of:
  a male member blind bore;
  a male member through bore; and
  a self-centering tip.

6. The bone fixation assembly of claim 1, wherein at least one of the male member and the female member comprises a bone retention feature.

7. The bone fixation assembly of claim 1, wherein:
the male member comprises a male member head having a first torque connection interface; and
the female member comprises a female member head having a second torque connection interface.

8. A bone fixation assembly comprising:
a male member, the male member comprising:
  a male member shaft comprising:
    a proximal end;
    a distal end; and
    a first longitudinal axis;
  a first bone engaging feature at the proximal end of the male member shaft;
  an external thread portion at the distal end of the male member shaft, the external thread portion having a first length and a first major diameter; and
  a male load-sharing feature intermediate the first bone engaging feature and the external thread portion, the male load-sharing feature having a second length and an outer diameter defining at least one male load-sharing surface; and a female member, the female member comprising:
  a female member shaft comprising:
    a proximal end;
    a distal end; and
    a second longitudinal axis;
  a second bone engaging feature at the proximal end of the female member shaft;
  an internal thread portion having a third length and a second major diameter, the internal thread portion configured to receive the external thread portion of the male member to removably couple the male member with the female member when the bone fixation assembly is implanted in a bone; and
  a female load-sharing feature located distal to the internal thread portion, the female load-sharing feature having a fourth length and an inner diameter defining at least one female load-sharing surface, the female load-sharing feature positioned and shaped to receive the male load-sharing feature therein;
  wherein, the outer diameter of the male load-sharing feature is greater than or equal to the first major diameter of the external thread portion.

9. The bone fixation assembly of claim 8, wherein:
the male member comprises a male member head having a first torque connection interface; and
the female member comprises a female member head having a second torque connection interface.

10. The bone fixation assembly of claim 9, wherein:
the male member head and the female member head comprise first partially spherical surfaces; and
the first bone engaging feature and the second bone engaging feature comprise second partially spherical surfaces configured to mate with the first partially spherical surfaces and allow polyaxial articulation of the first bone engaging feature and the second bone engaging feature with respect to the male member head and the female member head.

11. The bone fixation assembly of claim 10, wherein at least one of the first bone engaging feature and the second bone engaging feature comprises a washer.

12. The bone fixation assembly of claim 10, wherein:
at least one of the first bone engaging feature and the second bone engaging feature comprises a bone plate;
the bone fixation assembly further comprises a retention cap configured to couple with the bone plate; and
one or more retention surfaces of the retention cap are configured to engage with at least one of the male member head and the female member head to adjust a space between the first bone engaging feature and the second bone engaging feature.

13. The bone fixation assembly of claim 8, wherein the inner diameter of the female load sharing feature is greater than or equal to the second major diameter of the internal thread portion.

14. The bone fixation assembly of claim 8, wherein at least one of the at least one male load-sharing surface and the at least one female load-sharing surface comprises a cylindrical surface.

15. A bone fixation assembly comprising:
a male member formed of a rigid metal, the male member comprising:
  a male member shaft comprising:
    a proximal end;
    a distal end; and
    a first longitudinal axis;
  a first bone engaging feature at the proximal end of the male member shaft;

an external thread portion at the distal end of the male member shaft, the external thread portion having a first length and a first major diameter; and a male load-sharing feature intermediate the first bone engaging feature and the external thread portion, the male load-sharing feature having a second length and an outer diameter defining at least one male load-sharing surface; and a female member formed of a rigid metal, the female member comprising:

a female member shaft comprising:
a proximal end;
a distal end; and
a second longitudinal axis;

a second bone engaging feature at the proximal end of the female member shaft;

an internal thread portion having a third length and a second major diameter, the internal thread portion configured to receive the external thread portion of the male member to removably couple the male member with the female member; and a female load-sharing feature located distal to the internal thread portion, the female load-sharing feature having a fourth length and an inner diameter defining at least one female load-sharing surface, the female load-sharing feature positioned and shaped to receive the male load-sharing feature therein;

wherein, in response to a bending load acting on the bone fixation assembly after implantation in a bone, at least one of the male member and the female member bend such that, at least a portion of the at least one male load-sharing surface engages with at least a portion of the at least one female load-sharing surface to distribute the bending load between the male member and the female member.

16. The bone fixation assembly of claim 15, wherein at least one of the male member and the female member comprises a bone retention feature.

17. The bone fixation assembly of claim 16, wherein the bone retention feature comprises one or more barbs.

18. The bone fixation assembly of claim 16, wherein the bone retention feature comprises a thread.

19. The bone fixation assembly of claim 18, wherein the thread comprises at least one of a right-handed thread and a left-handed thread.

20. The bone fixation assembly of claim 18, wherein the inner diameter of the female load sharing feature is greater than or equal to the second major diameter of the internal thread portion.

* * * * *